US012616380B2

(12) United States Patent
Semenov

(10) Patent No.: US 12,616,380 B2
(45) Date of Patent: May 5, 2026

(54) ELECTROMAGNETIC TOMOGRAPHY AND TOMOGRAPHIC ANGIOGRAPHY

(71) Applicant: Serguei Semenov, Vienna (AT)

(72) Inventor: Serguei Semenov, Vienna (AT)

(73) Assignee: Serguei Semenov, Vienna (AT)

( * ) Notice: Subject to any disclaimer, the term of this patent is extended or adjusted under 35 U.S.C. 154(b) by 338 days.

(21) Appl. No.: 18/139,536

(22) Filed: Apr. 26, 2023

(65) Prior Publication Data

US 2023/0346229 A1     Nov. 2, 2023

Related U.S. Application Data

(60) Provisional application No. 63/473,061, filed on Apr. 27, 2022.

(51) Int. Cl.
| *A61B 5/02* | (2006.01) |
| *A61B 5/00* | (2006.01) |
| *A61B 5/0507* | (2021.01) |

(52) U.S. Cl.
CPC ........ *A61B 5/02007* (2013.01); *A61B 5/0507* (2013.01); *A61B 5/7292* (2013.01)

(58) Field of Classification Search
CPC . A61B 5/02007; A61B 5/0507; A61B 5/7292; A61B 5/0042; A61B 5/352; A61B 5/7285
See application file for complete search history.

(56) References Cited

U.S. PATENT DOCUMENTS

| 6,993,379 B1 | 1/2006 | Kroll et al. |
| 9,072,449 B2 | 7/2015 | Semenov |

| 9,414,749 B2 | 8/2016 | Semenov |
| 9,414,763 B2 | 8/2016 | Semenov |
| 9,414,764 B2 | 8/2016 | Semenov |
| 9,675,254 B2 | 6/2017 | Semenov |
| 9,675,255 B2 | 6/2017 | Semenov |
| 9,724,010 B2 | 8/2017 | Semenov |
| 9,924,873 B2 | 3/2018 | Semenov |
| 10,492,700 B2 | 12/2019 | Semenov |

(Continued)

OTHER PUBLICATIONS

Semenov S Y, Svenson R H and Tatsis G P "Microwave spectroscopy of myocardial ischemia and infarction. 1. Experimental study", Annals of Biomed. Eng, 2000, 28 48-54, 7 pages.

(Continued)

*Primary Examiner* — Sanjay Cattungal

(74) *Attorney, Agent, or Firm* — Potomac Law Group, PLLC; Amanda Y. Baker

(57) ABSTRACT

A method for tomographic imaging a dielectric object includes irradiating an object with electromagnetic radiation during a first time interval, receiving electromagnetic radiation passed through dielectric object to generate a first dataset at a plurality of spatial locations, irradiating the object with electromagnetic radiation during a second time interval, receiving electromagnetic radiation passed through dielectric object to generate a second dataset at a plurality of spatial locations, generating a third dataset, wherein the third dataset is determined as a function of the first dataset, the second dataset, and a normalized difference between the first dataset and the second dataset, and reconstructing a dielectric image of the object based on the third dataset.

14 Claims, 17 Drawing Sheets

(56) References Cited

U.S. PATENT DOCUMENTS

| | | | |
|---|---|---|---|
| 10,667,715 B2* | 6/2020 | Rappaport | A61B 5/05 |
| 10,921,361 B2 | 2/2021 | Semenov | |
| 10,980,421 B2 | 4/2021 | Semenov | |
| 10,980,435 B2 | 4/2021 | Semenov | |
| 11,253,164 B2 | 2/2022 | Semenov et al. | |
| 11,344,216 B2 | 5/2022 | Semenov et al. | |
| 11,350,842 B2 | 6/2022 | Semenov et al. | |
| 11,517,214 B2 | 12/2022 | Semenov | |
| 11,607,134 B2 | 3/2023 | Semenov | |
| 2012/0162002 A1* | 6/2012 | Semenov | A61B 5/053 342/22 |
| 2013/0158372 A1 | 6/2013 | Haisley et al. | |
| 2013/0171599 A1 | 7/2013 | Bleich et al. | |
| 2014/0155740 A1* | 6/2014 | Semenov | A61B 5/704 600/425 |
| 2014/0275944 A1 | 9/2014 | Semenov | |
| 2014/0276012 A1 | 9/2014 | Semenov | |
| 2015/0257648 A1 | 9/2015 | Semenov | |
| 2015/0257649 A1 | 9/2015 | Semenov | |
| 2016/0120469 A1 | 5/2016 | Freeman et al. | |
| 2016/0256109 A1 | 9/2016 | Semenov | |
| 2016/0262623 A1 | 9/2016 | Semenov | |
| 2016/0345856 A1 | 12/2016 | Semenov | |
| 2017/0238805 A1 | 8/2017 | Addison et al. | |
| 2017/0273563 A1 | 9/2017 | Semenov | |
| 2018/0231594 A1 | 8/2018 | Semenov | |
| 2018/0344165 A1 | 12/2018 | Semenov | |
| 2019/0274578 A1 | 9/2019 | Semenov et al. | |
| 2019/0307337 A1 | 10/2019 | Little et al. | |
| 2019/0357801 A1 | 11/2019 | Semenov et al. | |
| 2019/0357802 A1 | 11/2019 | Semenov et al. | |
| 2019/0357803 A1 | 11/2019 | Semenov et al. | |
| 2020/0170514 A1* | 6/2020 | Hui | A61B 5/1126 |
| 2021/0181246 A1 | 6/2021 | Semenov | |
| 2021/0228085 A1 | 7/2021 | Semenov | |
| 2021/0236008 A1 | 8/2021 | Semenov | |
| 2022/0296120 A1 | 9/2022 | Semenov et al. | |
| 2023/0116876 A1 | 4/2023 | Semenov | |

OTHER PUBLICATIONS

Semenov S Y, Svenson R H, Posukh V G, Nazarov A G, Sizov Y E, Kassel J and Tatsis G P "Dielectric spectroscopy of canine myocardium during ischemia and hypoxia at frequency spectrum from 100KHz to 6GHz", IEEE Trans. MI, 2002, 21 703-7, 5 pages.

Semenov S., Huynh T., Williams T., Nicholson B. and A. Vasilenko "Dielectric properties of brain tissue in acute ischemic stroke: experimental study on swine", Bioelectromagnetics, 2017, 38:158-163, DOI:10.1002/bem.22024, 6 pages.

Semenov S., Kellam J., Nair B., Sizov Y., Nazarov A., Williams T., Nair B., Pavlovsky A., Quinn M. "Microwave tomography of extremities: 2) Functional fused imaging of flow reduction and simulated compartment syndrome.", Phys. Med. Biol., 56 (2011) 2019-2030. Online at stacks.iop.org/PMB/56/2019. doi:10.1088/0031-9155/56/7/007, 13 pages.

Semenov S.Y. "Microwave Tomography: Review of the Progress towards Clinical applications", Phil. Trans. R. Soc. A, 2009 367, 3021-3042. doi: 10.1098/rsta.2009.0092, 23 pages.

Semenov S.Y., Kellam J.F., Althausen P., Williams T.C., Abubakar A., Bulyshev A., Sizov Y. "Microwave tomography for functional imaging of extremity soft tissues. Feasibility assessment", Phys. Med. Biol., 2007, 52, 5705-5719, 15 pages.

* cited by examiner

Figure 1A:
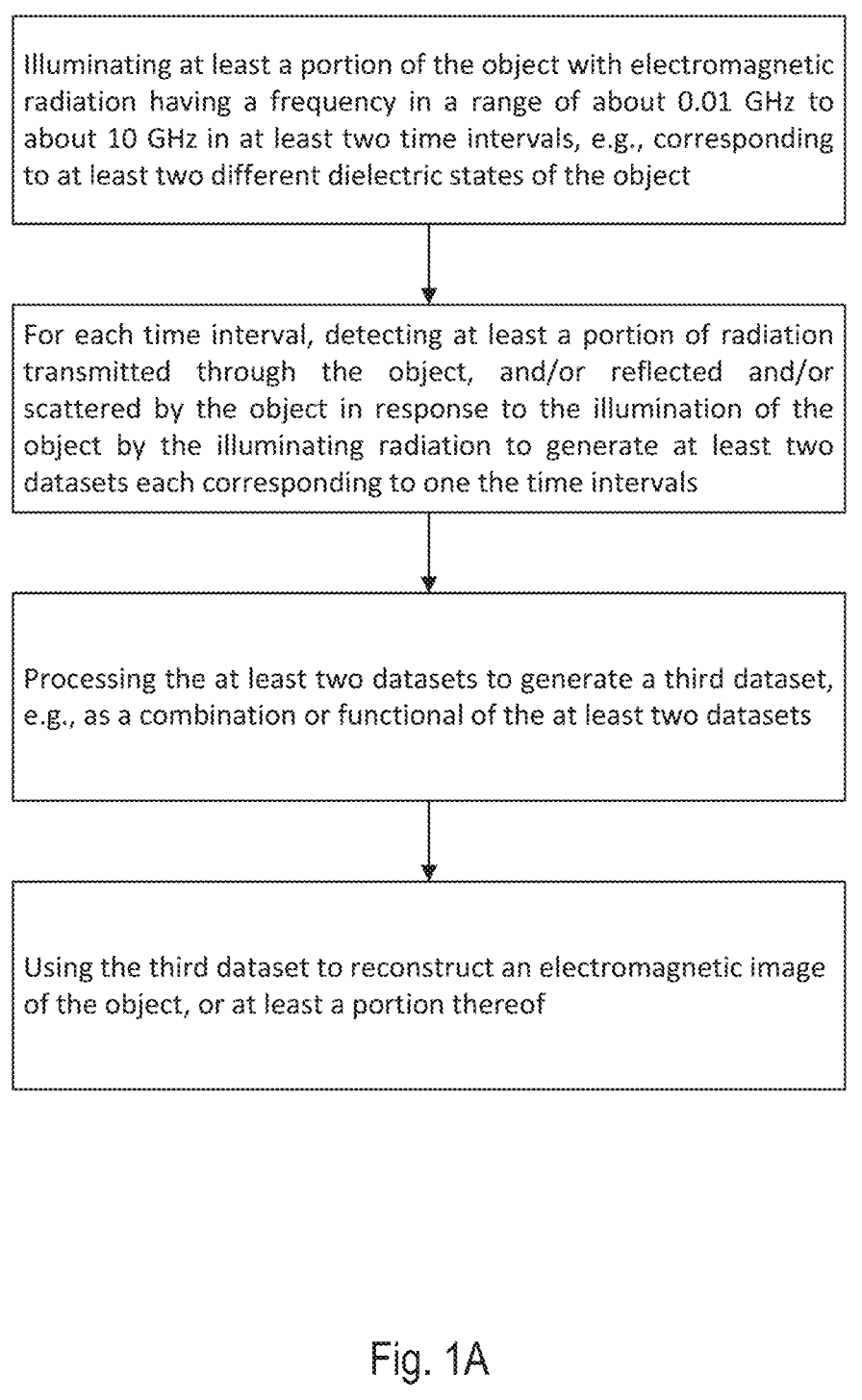

Illuminating at least a portion of the object with electromagnetic radiation having a frequency in a range of about 0.01 GHz to about 10 GHz in at least two time intervals, e.g., corresponding to at least two different dielectric states of the object For each time interval, detecting at least a portion of radiation transmitted through the object, and/or reflected and/or scattered by the object in response to the illumination of the object by the illuminating radiation to generate at least two datasets each corresponding to one the time intervals Processing the at least two datasets to generate a third dataset, e.g., as a combination or functional of the at least two datasets Using the third dataset to reconstruct an electromagnetic image of the object, or at least a portion thereof

Hypoxia

Ischemia
reversible

Ischemia
irreversible

Normal

TIME ⟹

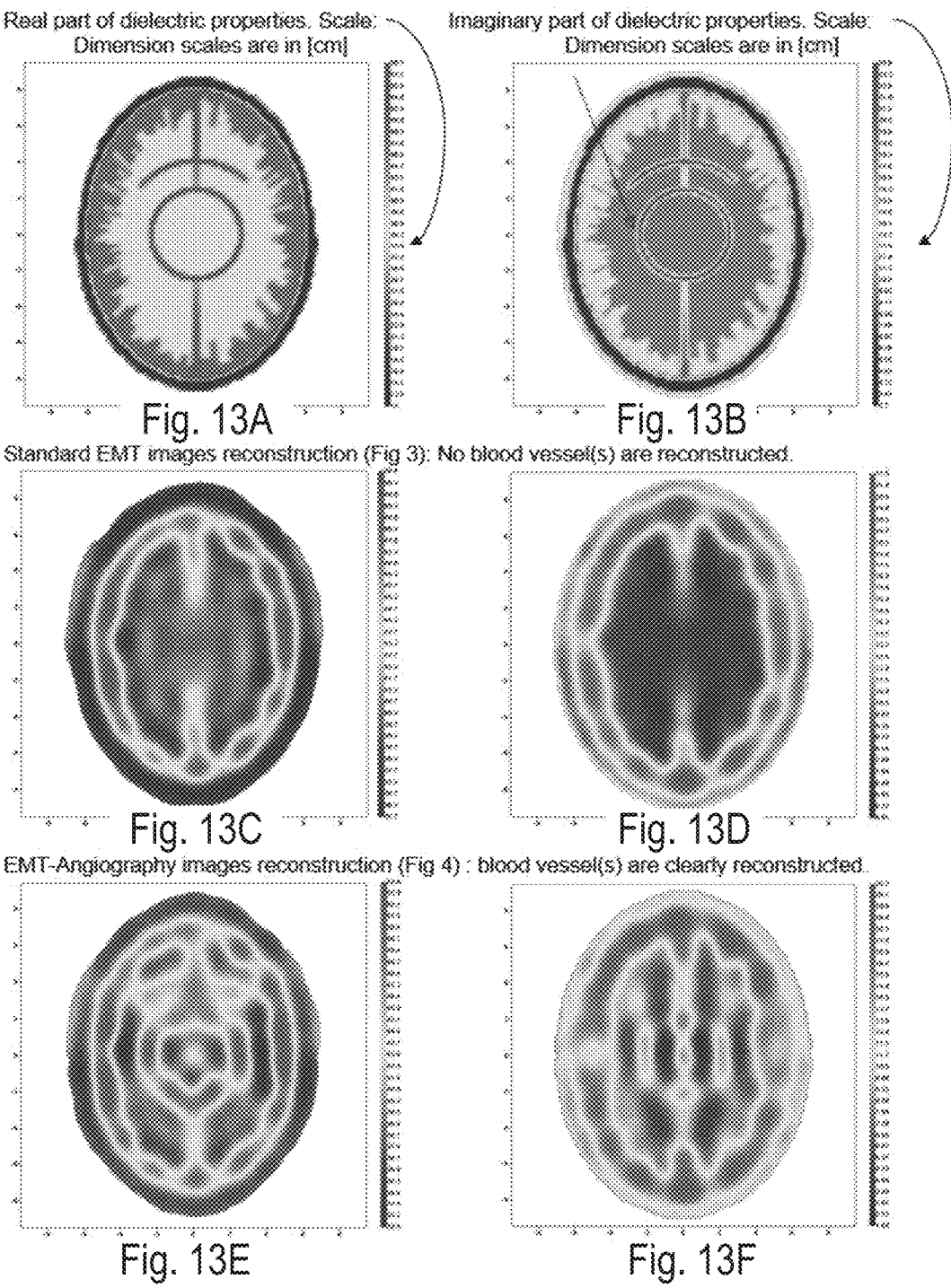

Target: virtual brain with blood vessels (including the circle of Willes). Typical diameter of a vessel is about 1.5-2.0mm.

Real part of dielectric properties. Scale: Dimension scales are in [cm]

Imaginary part of dielectric properties. Scale: Dimension scales are in [cm]

Fig. 13A          Fig. 13B

Standard EMT images reconstruction (Fig 3): No blood vessel(s) are reconstructed.

Fig. 13C          Fig. 13D

EMT-Angiography images reconstruction (Fig 4) : blood vessel(s) are clearly reconstructed.

Fig. 13E          Fig. 13F

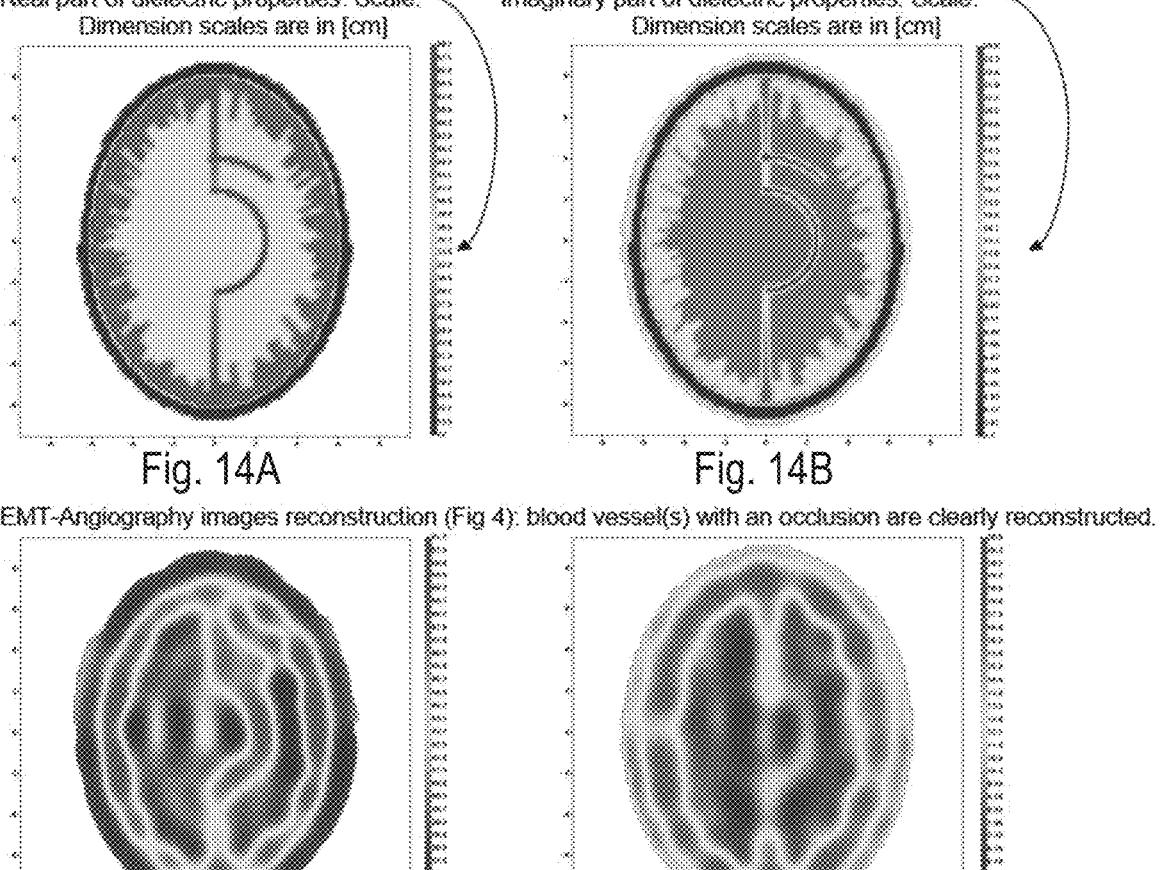

Target: virtual brain with a full occlusion of blood vessels (including the half circle of Willes) in one hemisphere Real part of dielectric properties. Scale:   Imaginary part of dielectric properties. Scale:
Dimension scales are in [cm]           Dimension scales are in [cm]

Fig. 14A                   Fig. 14B

EMT-Angiography images reconstruction (Fig 4): blood vessel(s) with an occlusion are clearly reconstructed.

Fig. 14C                   Fig. 14D

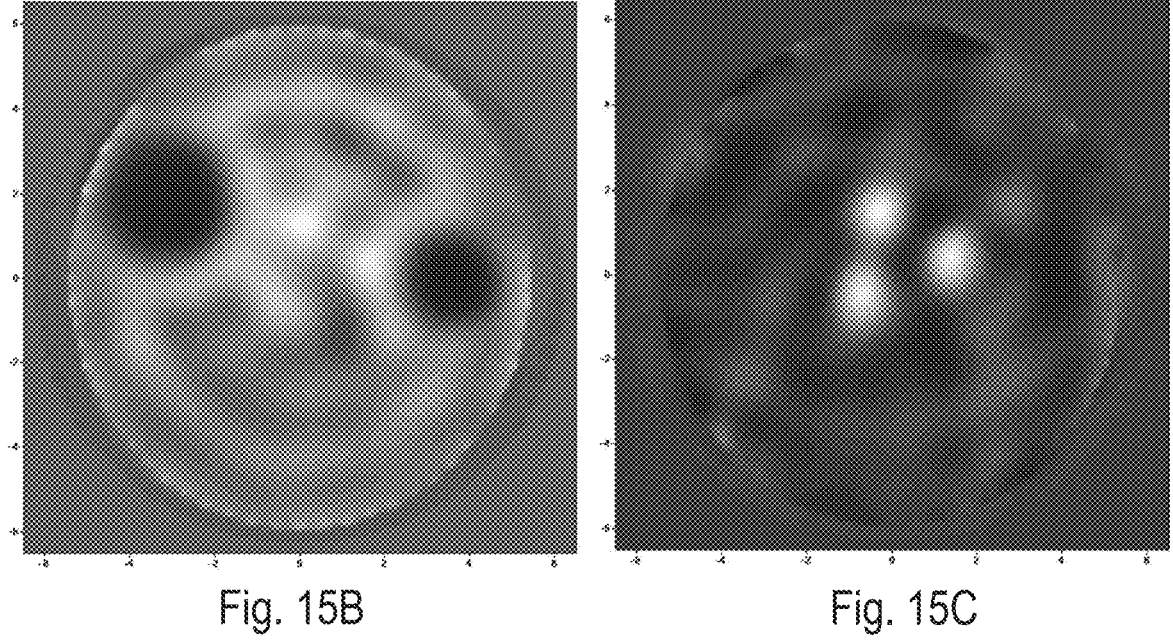
Fig. 15B                    Fig. 15C

ELECTROMAGNETIC TOMOGRAPHY AND TOMOGRAPHIC ANGIOGRAPHY

RELATED APPLICATIONS

The present application claims priority to a provisional application entitled Electromagnetic Tomography and Tomographic Angiography having application No. 63/473,061 filed on Apr. 27, 2022, which is incorporated by reference herein in its entirety.

TECHNICAL FIELD

The following relates to systems and methods for electromagnetic tomographic imaging of dielectric objects, including biological objects and their functional components, such as electromagnetic tomographic angiography of blood vessels of biological objects.

BACKGROUND

The present disclosure relates generally to tomographic imaging systems and angiography systems (both semi-static and movable), individually wearable systems, and related image reconstruction methods.

Electromagnetic tomography is a medical imaging technique which utilizes an electromagnetic radiation from non-ionizing portion of the electromagnetic spectrum (for example, in a frequency range of about 0.01 GHz to about 10 GHz) for interrogation of an object under study. In this portion of electromagnetic spectrum, tissues can be imaged based on their dielectric properties. For example, radiation in this frequency range can be employed to reconstruct a three-dimensional (3D) tomographic image of a biological object as, e.g., a 3D distribution of the dielectric properties of that object (e.g., a particular tissue portion).

Angiography or arteriography is a medical imaging technique used to visualize the inside, or lumen, of blood vessels and organs of the body, with particular interest in the arteries, veins, and the heart chambers. Such imaging is traditionally done by injecting a radio-opaque contrast agent into the blood vessel and imaging using X-ray based techniques such as fluoroscopy.

Standard-of-Care methods of angiography, such as X-Ray or CT- or MRI-angiography methods, are bulky, expensive and energy in-efficient. X-Ray and CT-angiography methods can be potentially hazardous as such techniques require the use of ionizing radiation.

Above mentioned standard-of-care methods of angiography are unable to provide on-line, safe, cost and energy efficient assessment of both tissue viability and status of vessels especially in mobile or wearable settings. This data might be of critical importance for example, during medical emergencies, at high-load physical conditions (athletes, pilots, etc.), at nursing homes, during anesthesia, surgery or childbirth, to name a few. Therefore, there is a need for a technology that is capable of addressing such issues of critical importance.

Electromagnetic tomography is applicable to functional imaging of biological objects in mobile and even wearable settings but suffers from a limited spatial resolution because of relatively large wavelength of radiation as compared to sizes of biological targets of particular interest, such as, for example blood vessels. For example, a wavelength of electromagnetic radiation at a typical frequency of 1 GHz, used for cerebral imaging is about 4.7 cm within a brain tissue, which is significantly larger than the dimensions of cerebral vessels.

SUMMARY

According to one or more aspects, the present disclosure relates to systems and methods for electromagnetic tomography (EMT) including electromagnetic tomographic Angiography (EMTA). In various embodiments, such systems and methods allow for i) EMT of any non-metal-covered dielectric objects, including but not limited to a) imaging of biological objects or parts of biological objects, such as human head or human torso or human extremity; b) imaging of crude oil in oil pipes or an assessment of a composition of oil-water-salt suspensions in desalters of oil refineries or an assessment of oil-refined products in refinery columns; ii) cerebral, cardiac and musculoskeletal EMT Angiography and iii) non-invasive assessment of tissue hypoxia and viability status of biological tissues, including but not limited to brain tissue, cardiac tissue and musculoskeletal tissue.

In one aspect, the present disclosure is directed to systems and methods for electromagnetic tomography including its applications in electromagnetic tomographic angiography as discussed in more detail below.

In some embodiments, such methods and systems for performing electromagnetic tomography and electromagnetic tomographic angiography can include: i) computational means, comprising at least the following; processor, memory storage, RAM, I/O interface and network adapter; ii) analog-to-digital converter (ADC) for digitizing acquired EM signals from electromagnetic (for example, but not limited to, RF or MW) measurement systems; iii) cardiac activity recording system, for example, but not limited to, ECG recording system with ADC for digitizing acquired ECG signals (typically in biomedical applications); iv) synchronization means for synchronization of acquisition of EM signals and cardiac activity signals, for example ECG signals (typically in biomedical applications); v) processing means for processing of implemented (for example, but not limited to, software executable modules or firmware or ASIC based implementations) imaging and processing algorithms as further described in detail below; vi) receiving complex electromagnetic signals (for example, amplitude and phase) from any suitable electromagnetic (RF or microwave) measurement system capable of measuring complex electromagnetic signals from, e.g., a plurality of antennas (sensors) e.g., located at known spatial locations (Ri) inside, and/or on the surface and/or outside of an object e.g., by receiving means located in both "Electromagnetic Tomography" and "Electromagnetic Angiography" blocks; vii) receiving information/data associated with cardiac activity, for example (but not limited to), from digitized ECG signal(s) from "ECG system plus ADC block" (typically in biomedical applications of the method); viii) synchronizing an acquisition of complex electromagnetic signals with cardiac activity from measured, for example, but not limited to, ECG recording generated, for example, by "ECG system plus ADC block" (typically in biomedical applications of the method); ix) providing a reconstruction of either 3D and/or 2D images of the dielectric property $(\varepsilon(r)_{updated})$ and/or either 4D and/or 3D movies $\varepsilon(r, time)_{updated}$ of dielectric properties of an object under study; x) providing a reconstruction of either 3D and/or 2D angiographic-dielectric images $\varepsilon(r)_{updated}$ and/or either 4D and/or 3D angiographic movies $\varepsilon(r, time)_{updated}$ of an object under study (typically in biomedical applications); xi) delivering reconstructed dielectric and/or angiographic-dielectric images and/or movies to end-users and memory storage; xii) post-processing of reconstructed dielectric and/or angiographic-dielectric images and/or movies for an assessment of hypoxia and viability of biological tissues (typically in biomedical applications of the method); and xiii) delivering the results of post-processing analysis to end-users and memory storage.

In a related aspect, a method of electromagnetic tomography can include: i) receiving complex electromagnetic signals (for example amplitude and phase) from any suitable electromagnetic (RF or microwave) measurement system capable of measuring complex electromagnetic signals, e.g., signals generated by a plurality of antennas (sensors), e.g., located at known spatial locations (Ri) inside, and/or on the surface and/or outside of an object by a receiver; ii) digitizing the received complex electromagnetic signals in an Analog-to-Digital converter (ADC) located, e.g., in a receiver of the electromagnetic measurement system; iii) receiving information associated with cardiac activity, for example, but not limited to, a digitized ECG signal generated, for example, by an "ECG system plus ADC block" (typically in biomedical applications); iv) setting-up and controlling measurements hardware of the electromagnetic (RF or microwave) measurement system; v) synchronizing acquisition of complex electromagnetic signals with cardiac activity from measured, for example, but not limited to, data in the form of ECG recording generated by the "ECG system plus ADC block" or cardiac data with time-flags stored in memory (typically in biomedical applications of the method); vi) using raw data acquired from electromagnetic measurement system to form a matrix of complex EM fields (for example: amplitude and phase) from N transmitters (or transceivers operating in transmit mode) measured on M receivers (or transceivers operating in receipt mode) (M*N matrix)–$Sij^{EXP}$, i=1, N; j=1, M; vii) calibrating and forming a calibrated M*N matrix of calibrated $Sij^{EXP}$ experimental data; viii) applying a method (including iterative methods) to reconstruct an image as described in ix)-xv) below; ix) using an "initial guess" as an initial distribution of dielectric properties $\varepsilon_1(r)$ at $1^{st}$ iteration, for example, but not limited to, a homogeneous distribution of dielectric properties $\varepsilon_1(r)=\varepsilon_0$, where $\varepsilon_0$ is, for example, but not limited to, a known dielectric property outside of an object under study, but inside of an imaging domain); x) calculating electromagnetic (EM) fields distribution from N (i=1, N) transceivers within the study domain $E_i(\varepsilon_k(r))$ and on M (j=1, M) receivers $Sij^{THR}$ at $k^{th}$ iteration (k=1,K); xi) calculating alteration $\Delta(\varepsilon=(r))$ using, e.g., gradient or/and Newton type of methods in the form of: a) for gradient $\Delta(\varepsilon(r))\sim\Sigma_{i,j}^{N,M}(E_i^*(\varepsilon_k(r))\times E_j(\varepsilon_k(r))\times(Sij^{THR}-Sij^{EXP})$, and b) for Newton $\Delta(\varepsilon(r))\sim$inversion of the matrix Dij=$(E_i^*(\varepsilon_k(r))\times E_j(\varepsilon_k(r)))$; xii) updating the distribution of dielectric properties within the study domain at iteration k as $\varepsilon(r)_{updated}=\varepsilon_{k-1}(r)+\Delta(\varepsilon(r))$—this corresponds to an updated image; xiii) making decision: if $\varepsilon(r)_{updated}$ satisfies predefined criteria, then reconstructed image $\varepsilon(r)_{updated}$ is considered as being generated and can be displayed to a user or it can be subjected to further post-processing and analysis, and the reconstructed image can be stored in memory; xiv) making decision: if $\varepsilon(r)_{updated}$ does not satisfy the predefined criteria, then the reconstructed image $\varepsilon(r)_{updated}$ is subjected to the next iteration cycle.

By way of example, and without limitation, the predefined criteria can be based on the satisfaction of the following relation at iteration k: $\Sigma_{i,j}^{N,M}|(Sij^{THR\_iter=k}-Sij^{EXP})|<$ $\beta*\Sigma_{i,j}^{N,M}|(Sij^{THR\_iter=1}-Sij^{EXP})|$, where |A| is a norm of complex A and $\beta$ is a convergence accuracy parameter. By way of example, in various embodiments, the convergence accuracy parameter can be in a range of about 0.9 to about 0.99, e.g., about 0.95; xv) making multiple reconstructed images over time (for example, but not limited to synchronized with ECG), so the images may be used as frames to compile a movie (optional); xvi) providing input and control parameters and calculation flow control by "Input and calculation flow control" means, and xvii) storing electromagnetic measurements data, and optionally cardiac activity data (for example, but not limited to ECG data) and reconstructed images $\varepsilon(r)_{updated}$ in memory.

In another aspect, a method of electromagnetic tomographic angiography includes (typically in biomedical applications): i) receiving complex electromagnetic signals (for example amplitude and phase) from, e.g., an electromagnetic (e.g., RF or microwave) measurement system that is capable of measuring complex electromagnetic signals generated by a plurality of antennas (sensors) located at known spatial locations (Ri) inside, and/or on the surface and/or outside of an object, e.g., by receiving means; ii) digitizing received complex electromagnetic signals, e.g., in an Analog-to-Digital converter (ADC) located, e.g., in receiving means; iii) receiving information of cardiac activity, for example, but not limited to, from digitized ECG signal, e.g., from "ECG system plus ADC block"; iv) setting-up and controlling measurements hardware of electromagnetic (RF or microwave) measurement system; v) synchronizing an acquisition of complex electromagnetic signals with cardiac activity from measured, for example, but not limited to, data in the form of ECG recording by, e.g., "ECG system plus ADC block" or cardiac data with time-flags stored in memory; vi) choosing at least two phases of interest from cardiac activity cycle, for example, but not limited to, phases of systole and diastole; vii) using raw experimental data acquired from electromagnetic measurements system during phase of interest No. 1 (e.g., the systolic phase of the cardiac cycle), forming a matrix of complex EM fields, (for example, amplitude and phase) from N transceivers measured on M receivers (M*N matrix)–$Sij^{EXP-1}$, i=1, N; j=1, M; vii), calibrating and forming an M*N matrix of calibrated $Sij^{EXP-1}$ phase 1 experimental data, viii) using raw experimental data acquired from electromagnetic measurements system during phase of interest No. 2 (e.g., the diastolic phase of the cardiac cycle), forming a matrix of complex EM fields (for example: amplitude and phase) from N transceivers measured on M receivers (M*N matrix)–$Sij^{EXP-2}$, i=1, N; j=1, M; ix), calibrating and forming a M*N matrix of calibrated $Sij^{EXP-2}$ phase 2 experimental data; x) Calculating a perturbated M*N matrix of $Sij^{EXP\ 1/2}$ in the form of, for example, but not limited to: $Sij^{EXP\ 1/2}=Sij^{EXP-1}+\alpha(Sij^{EXP-1}-Sij^{EXP-2})/|Sij^{EXP-1}|$, where $|Sij^{EXP-1}|$ is a norm of complex $Sij^{EXP-1}$ and $\alpha$—is a parameter chosen by a trial method; xi) applying an iterative method to reconstruct an image as described in xii)-xvii) below, xii) using an "initial guess" as an initial distribution of dielectric properties $\varepsilon_1(r)$ at $1^{st}$ iteration, for example, but not limited to, a homogeneous distribution of dielectric properties $\varepsilon_1(r)=\varepsilon_0$, where $\varepsilon_0$ is, for example, but not limited to, known dielectric properties of outside of an object under study, but inside of an imaging domain); xiii) calculating electromagnetic (EM) fields distribution from N (i=1, N) transceivers within the study domain $E_i(\varepsilon_k(r))$ and on M (j=1, M) receivers $Sij^{THR}$ at $k^{th}$ iteration (k=1,K); xiv) calculating an alteration $\Delta(\varepsilon(r))$ using gradient or/and Newton type of methods in the form of: a) for gradient $\Delta(\varepsilon(r))\sim\Sigma_{i,j}^{N,M}(E_i^*(\varepsilon_k(r))\times E_j^*(\varepsilon_k(r))\times(Sij^{THR}-Sij^{EXP\ 1/2})$ b) for Newton $\Delta(\varepsilon(r))\sim$inversion of the matrix Dij=$(E_i^*(\varepsilon_k(r))\times E_j(\varepsilon_k(r)))$; xv) updating the distribution of dielectric properties within the study domain at iteration k as $\varepsilon(t)_{updated} = \varepsilon_{k-1}(r) + \Delta(\varepsilon(r))$—this is an updated angio-dielectric image; xvi) making decision: if $\varepsilon(r)_{updated}$ satisfies decision making criteria, then the reconstructed angio-dielectric image $\varepsilon(r)_{updated}$ can be presented to either end-users and/or be subjected to further post-processing and analysis and be stored in memory; xvii) making decision: if $\varepsilon(r)_{updated}$ does not satisfy decision making criteria, the reconstructed angio-dielectric image $\varepsilon(r)_{updated}$ can be taken to the next iteration cycle; xvi) making multiple reconstructed images over time, for example, but not limited to synchronized with ECG, so the images might be used as frames to compile a movie (optional).

In some embodiments, the decision criteria can be based, e.g., on the satisfaction of the following (for example, but not limited to) at iteration k: $\Sigma_{i,j}^{N,M}|(Sij^{THR\_iter=k}-Sij^{EXP})| < \beta * \Sigma_{i,j}^{N,M}|(Sij^{THR\_iter=1}-Sij^{EXP})|$, where $|A|$ denotes a norm of complex A and $\beta$ is a convergence accuracy parameter, for example, but not limited to a range of about 0.90 to about 0.99, e.g., 0.95, providing input and control parameters and calculation flow control by "Input and calculation flow control" means, storing electromagnetic measurements data, cardiac activity data (for example, but not limited to ECG data) and reconstructed angio-dielectric images $\varepsilon(r)_{updated}$ in memory.

In yet another aspect, a method of postprocessing of reconstructed images $\varepsilon(r)_{updated}$ for an assessment of oxygenation status and viability of biological tissue (as illustrated in FIG. 8), includes (typically in biomedical applications of the method): i) receiving reconstructed dielectric images $\varepsilon(r)^d_{updated}$, e.g., from Electromagnetic Tomography block and/or reconstructed angio-dielectric images $\varepsilon(r)^{ad}_{updated}$, e.g., from Electromagnetic Tomographic Angiography block; ii) receiving cardiac data, e.g., either directly from ECG+ADC system or from memory in the form of, for example, but not limited to, digitized ECG; iii) synchronizing a time of acquisition of raw electromagnetic data used to reconstruct images with cardiac activity from measured (for example, but not limited to) data in the form of ECG recording, e.g., by "ECG system plus ADC block" or cardiac data with time-flags stored in memory; iv) providing a dynamic cross-correlation analysis of region(s) of spatial interest within $\varepsilon(r, time)^d$ and/or $\varepsilon(r)^{ad}_{updated}$ with ECG(time) by computing the following:

$$\sum_{i=1+k}^{M+k} E_i \times (E_i - E_{mean}) \times (F_i - F_{mean}) / \left( \sqrt{\sum_{i=1+k}^{M+k}(E_i - E_{mean})^2} \times \sqrt{\sum_{i=1+k}^{M+k}(F_i - F_{mean})^2} \right)$$

wherein, $E_i$ denotes an $i^{th}$ reading of $\varepsilon(r, i^{th}$ time reading)$^d_{updated}$ or $\varepsilon(r, i^{th}$ time reading)$^{ad}_{updated}$ at spatial point (x,y,z) of interest, $E_{mean}$ denotes a mean of $E_i$ over k-time points; $F_i$ denotes an $i^{th}$ reading of digitized physiological data signal (for example, but not limited to digitized ECG signal) and $F_{mean}$ denotes a mean of the physiological data over k-time points, v) providing a dynamic DC-component analysis of region(s) of spatial interest within $\varepsilon(r, time)^d$ and/or $\varepsilon(r)^{ad}_{updated}$ with ECG(time); vi) delivering the results of analysis to End users and store the results in memory.

In yet another aspect, a system for electromagnetic tomography and electromagnetic tomographic angiography includes: i) computational means, comprising at least the following: processor, memory storage, RAM, I/O interface and network adapter; ii) analog-to-digital converter (ADC) for digitizing acquired EM signals from electromagnetic (for example, but not limited to, RF or MW) measurements system; iii) cardiac activity recording system (for example, but not limited to) ECG recording system with ADC for digitizing acquired ECG signals (typically in biomedical applications); iv) synchronization means, for synchronization of acquisition of EM signals and cardiac activity signals, for example ECG signals (typically in biomedical applications), v) processing means for processing of implemented (for example, but not limited to as software executable modules or firmware or ASIC based implementation) imaging and processing algorithms as described herein.

In a related aspect, a method for imaging a dielectric object exhibiting at least two dielectric states (or a component/part of an object exhibiting at least two dielectric states) having different dielectric properties is disclosed, which includes for each state of the object, illuminating at least a portion of the object with electromagnetic radiation having a frequency in a range of about 0.01 GHz to about 10 GHz, where the frequency corresponds to a wavelength of the radiation within the object that is greater than at least one of a size of the object in at least one spatial dimension and a dielectric inhomogeneity within the object, detecting at least a portion of the electromagnetic radiation transmitted through the object, reflected, diffracted or scattered from the object in response to the illumination to generate a first detected signal dataset corresponding to one of the dielectric states and to generate a second detected signal dataset corresponding to the other dielectric state, and using a digital data processor to generate a dielectric image of the object based on combined information in the first and the second datasets such that the dielectric image exhibits a spatial resolution characterized by a size less than a size associated with a spatial resolution that can be achieved when only one of the datasets is employed. In other words, the use of the multiple datasets as disclosed herein for generating a dielectric image of an object or a portion thereof results in achieving a better spatial resolution that could be achieved using only one of those datasets. The size associated with an achieved spatial resolution is generally less than the wavelength of the electromagnetic radiation within the object or a portion of the object that is being imaged.

The dielectric image can provide a spatial map of the complex dielectric properties of the object, that is, the image can provide the real and imaginary parts of the dielectric permittivity of the object at a plurality of locations in the object.

In some embodiments, the object can be a biological object, e.g., a vessel, such as a heart or cerebral vessel. In some such embodiments, the different states of the object can correspond to different phases of cardiac activity, e.g., the systolic and the diastolic phases of the cardiac cycle. By way of example, at least a signal associated with an electrocardiogram to synchronize acquisition of the first and the second datasets with the diastolic and systolic phases of cardiac activity.

In some embodiments, the object can include a tubular structure providing a lumen through which a fluid can flow. In some such embodiments, the two dielectric states can correspond to different flow volume or dielectric composition of the fluid through the lumen. The tubular structure can have a flexible wall that exhibits different flexures in response to said different flow volume or composition of the fluid.

In a related aspect, a method for imaging a dielectric object is disclosed, which includes irradiating an object with a first radiation during a first time interval, where the first radiation has a frequency in a range of about 0.01 GHz to about 10 GHz and corresponds to a wavelength of the radiation within the object that is greater than at least one of a size of the object in at least one spatial dimension and a dielectric inhomogeneity within the object, detecting electromagnetic radiation transmitted through the object, reflected, diffracted or scattered by the object in response to the illumination to generate a first signal dataset, irradiating the object with a second radiation during a second time interval, wherein the second radiation has a frequency in a range of about 0.01 GHz to about 10 GHz and wherein the radiation frequency corresponds to a wavelength within the object that is greater than at least one of the size of the object in the at least one spatial dimension and the dielectric inhomogeneity within the object.

At least a portion of the electromagnetic radiation transmitted through the object, reflected, diffracted or scattered by the object in response to illumination by the second radiation can be detected to generate a second signal dataset. A digital data processor can be used to generate a dielectric image of the object based on combined information in the first and the second datasets such that the dielectric image exhibits a spatial resolution characterized by a size less than the wavelength of the electromagnetic radiation within the object. The dielectric image can be represented by a set of complex values of dielectric values associated with different locations of the object, where the real and the imaginary parts of the complex values correspond to the real and imaginary parts of the dielectric properties, respectively.

In some embodiments, the second and the first radiation frequencies are substantially equal. In other embodiments, the first and the second radiation frequencies may be different. In such embodiments in which different radiation frequencies are employed for generating the first and the second datasets, the dispersion of the dielectric properties of the object (e.g., tissue), i.e., the dependence of the object dielectric permittivity from frequency, should be taken into account in reconstructing the dielectric image. The dispersion might be taken into account using Debye type approximation of tissue dielectric properties at radio- to microwave frequency band, for example as:

$$\varepsilon_{tissue} = \varepsilon_{iR} + (\varepsilon_0 - \varepsilon_{iR}) * \sum_{n=1}^{N} \frac{K_n}{\left\{1 + i\frac{f}{f_n}\right\}} + i\frac{\sigma_{ion}}{\alpha * f}$$

Where: f—frequency, N=3—in the case of taking into account free water, bound water and protein relaxations; $i^2=-1$; $K_n$ and $f_n$—are volume fraction and relaxation frequency of free water, bound water and proteins; $\varepsilon_0$ and $\varepsilon_{iR}$—are permittivity at low and high (IR) frequencies; $\sigma_{ion}$—ion conductivity; $\alpha$—coefficient. The parameters in this equation are tissue-specific, but range of their values is known and will be tuned up during iterative reconstruction process. In the case of a small frequency variations, such as less than 10 MHz, the tissue dispersion can be neglected.

In some embodiments, one or more synchronization signals can be used to synchronize acquisition of any of the first and second datasets with different states of the object.

By way of example, in some embodiments, the object can be in the form of a tubular structure through which a fluid can flow. In some such cases, the tubular structure can have a flexible wall such that the flow of the fluid can cause a flexure of the wall. The different states of such a tubular structure can correspond, for example, to different flow volume of the fluid through the tubular structure.

In some embodiments, the object can be a biological object, e.g., a vessel such as a coronary or cerebral vessel. In some such cases, the different phases (states) of the vessel can correspond to different phases of cardiac activity. For example, in some embodiments, EM datasets associated with the object at different portions of a cardiac cycle can be acquired and analyzed in accordance with the present teachings. For example, one dataset can correspond to the systolic phase of the cardiac cycle and another dataset can correspond to the diastolic phase of the cardiac cycle.

As noted above, in some embodiments, a dielectric image of a biological object acquired using methods and systems according to the present teachings can be further analyzed to assess viability of the biological object. By way of example, the dielectric image can be analyzed to determine the level of oxygenation, which can in turn provide an indication of viability of the tissue. By way of example, the assessment of the oxygenation level of the biological object can be achieved via computing one or more cross-correlations between different regions of the dielectric image at different cardiac phases.

In a related aspect, a system for imaging a dielectric object of interest is disclosed, which comprises an imaging system configured to generate imaging data associated with an object, a synchronization system in communication with the imaging system for generating one or more synchronization signals and transmitting the one or more synchronization signals to the imaging system for synchronizing generation of imaging data with one or more phases of the object. The system can further include a data processing and analysis module in communication with the imaging system for receiving a plurality of imaging datasets each corresponding to the one or more phases of the object and generating a dielectric image of the object based on combined information in the imaging datasets such that the dielectric image exhibits a spatial resolution characterized by a size less than the wavelength of the electromagnetic radiation within the object, i.e., a spatial resolution less than about 2 mm, e.g., in a range of about 1 mm to about 2 mm.

In some embodiments, the object can be a biological object, such as a vessel, and the synchronization system can be configured to generate synchronization signals corresponding to different phases of a subject's cardiac cycle, such as the systolic and the diastolic phases of the cardiac cycle.

In some embodiments, the object can be a tissue portion and the data processing and analysis module can be further configured to process the dielectric image to assess oxygenation level of the tissue portion, e.g., for assessing the viability of the tissue portion.

In one aspect, a method for tomographic imaging at least a portion of a dielectric object exhibiting at least two dielectric states having different dielectric properties, includes for each state of the at least a portion of the dielectric object, illuminating said at least a portion of the dielectric object with electromagnetic radiation having a frequency in a range of about 0.01 GHz to about 10 GHz, detecting electromagnetic radiation transmitted, reflected, diffracted or scattered from the object in response to the illumination to generate at least a first detected signal dataset corresponding to one of the dielectric states and to generate at least a second detected signal dataset corresponding to the other state, and using a digital data processor to reconstruct a dielectric image associated with a plurality of spatial locations within an imaging domain of the least a portion of the object based on combined information from at least the first and the at least the second dataset such that the dielectric image of said at least a portion of the object exhibits a spatial resolution characterized by a size less than the wavelength of the electromagnetic radiation within the at least a portion of the object.

In some embodiments the method further includes compiling a first and second matrix of raw data required for tomographic imaging. In some embodiments, the reconstructed dielectric image provides complex values of dielectric permittivity of the object at spatial locations within said imaging domain. In some embodiments, the object comprises a biological object with vasculature. In some embodiments, the vasculature comprises any of a coronary or a cerebral vessel and one of the states corresponds to a diastolic phase and the other state corresponds to a systolic phase of cardiac activity. In some embodiments, the method further comprises utilizing at least a signal associated with an electrocardiogram to synchronize acquisition of the first and second datasets with the diastolic and the systolic phases of cardiac activity. In some embodiments, the object comprises a tubular structure providing a lumen through which a fluid flows. In some embodiments, the two dielectric states correspond to different flow volumes or dielectric compositions of the fluid through said lumen. In some embodiments the tubular structure has a flexible wall that exhibits different flexures in response to said different flow volumes of the fluid.

In another aspect a method for tomographic imaging a dielectric object includes irradiating an object with a first radiation during a first time interval, wherein the first radiation has a frequency in a range of about 0.01 GHz to about 10 GHz, detecting electromagnetic radiation transmitted through the object, reflected, diffracted or scattered by the object in response to the illumination to generate a first signal dataset, irradiating the object with a second radiation during a second time interval, wherein the second radiation has a frequency in a range of about 0.01 GHz to about 10 GHz, detecting electromagnetic radiation transmitted through the object, reflected, diffracted or scattered by the object in response to the second radiation to generate a second signal dataset, and using a digital data processor to generate a dielectric image of the object based on combined information in the first and the second dataset such that the dielectric image exhibits a spatial resolution characterized by a size less than the wavelength of the electromagnetic radiation within the object.

In some embodiments the method further includes using one or more radiation cycles required to compile a matrix of raw tomographic data, compiling a first matrix of raw data, and compiling a second matrix of raw data. In some embodiments, the dielectric image provides complex values of dielectric permittivity of the object at a plurality of spatial locations. In some embodiments a real portion and an imaginary portion of each of the complex values corresponds, respectively, to real and imaginary part of the dielectric permittivity. In some embodiments, the object comprises a biological object. In some embodiments, biological object comprises a vessel. In some embodiments, the vessel comprises any of a coronary and a cerebral vessel. In some embodiments, the method further includes utilizing at least one synchronization signal to synchronize acquisition of any of said first and second datasets with different states of said object. In some embodiments, the object comprises a tubular structure providing a lumen through which a fluid flows. In some embodiments, the two dielectric states correspond to different flow volume of the fluid through said lumen. In some embodiments, the tubular structure has a flexible wall that exhibits different flexures in response to said different flow volume of the fluid. In some embodiments, said biological object comprises tissue. In some embodiments, the method further includes comprising utilizing said reconstructed dielectric image to assess any of viability and oxygenation of said tissue.

In another aspect, a system for tomographic imaging at least a portion of dielectric object of interest, includes an imaging system configured to reconstruct an image of said at least a portion of the dielectric object, a synchronization system in communication with the imaging system for generating one or more synchronization signals and transmitting said one or more synchronization signals to said imaging system for synchronizing generation of imaging data with one or more phases of said object, and a data processing and analysis module in communication with said imaging system for receiving a plurality of electromagnetic signal datasets each corresponding to one of said one or more phases of said object and generating a dielectric image of the object based on combined information in said electromagnetic signal datasets such that the reconstructed dielectric image exhibits a spatial resolution of the at least a portion of the object, wherein said spatial resolution is characterized by a size less than the wavelength of the electromagnetic radiation within the object. In some embodiments, the object comprises a biological object with vasculature. In some embodiments, the synchronization system is configured to generate synchronization signals corresponding to different phases of a subject's cardiac activity. In some embodiments, the different phases of the subject's cardiac activity comprises systolic and diastolic phases of the subject's cardiac cycle. In some embodiments, the object is a tissue portion and said data processing and analysis module is further configured to process said dielectric image to assess any of viability and oxygenation of said tissue portion.

Further understanding of various aspects of the present teachings can be obtained by reference to the following detailed description in conjunction with the associated drawings, which are described briefly below.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description take in conjunction with the accompanying drawings in which:

FIG. 1A schematically is a flow chart depicting various steps according to an embodiment of the present teachings.

FIG. 13A provides a map of the real part of the dielectric permittivity of a virtual model of human brain with blood vessels (including the circle of Willes);

FIG. 13B provides a map of the imaginary part of the dielectric permittivity of the virtual model of brain with blood vessels (including the circle of Willes);

FIGS. 13C and 13D show EMT images of the real and the imaginary parts of the dielectric permittivity of the virtual model of human brain generated using conventional image reconstruction methods;

FIGS. 13E and 13F show EMT-angiography images of the real and imaginary parts of the dielectric permittivity of virtual model of human brain, which were reconstructed using embodiments of the present teachings;

FIGS. 14A and 14B show maps of the real and the imaginary parts of the dielectric permittivity of a virtual model of a human brain with a full occlusion of blood vessels (including the half circle of Willes) in one hemisphere;

FIGS. 14C and 14D show EMT-Angiography images corresponding to the real and the imaginary parts of the dielectric permittivity that are reconstructed using an embodiment of the present teachings.

FIG. 15B shows EMT-Angiography image corresponding to the real part of the dielectric permittivity that are reconstructed using an embodiment of the present teachings.

FIG. 15C shows differential EMT-Angiography image corresponding to the differences between i) the reconstructed image when all vessels are in function (normal vessel function—FIG. 15B) and ii) the reconstructed image when arteries are in normal function but vein are blocked (because of the rise of compartmental pressure) that are reconstructed using an embodiment of the present teachings.

DETAILED DESCRIPTION

Figure 1B:
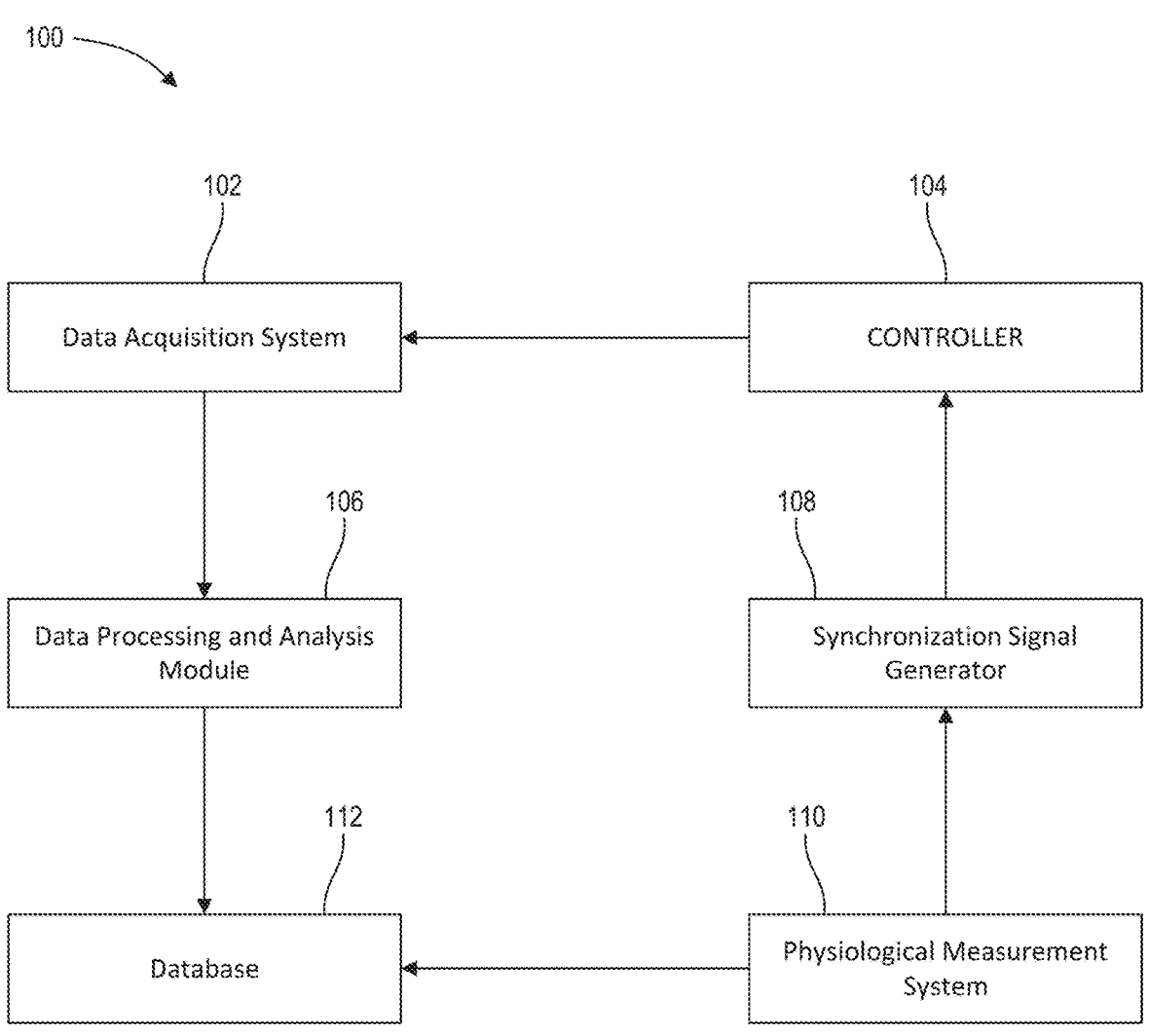
FIG. 1B is a schematic view of a system according to an embodiment of the present teachings, FIG. 2A schematically depicts an example of one transmitter-to-one receiver portion of an EM measurement system suitable for use in various embodiments of the present teachings, FIG. 2B schematically depicts an example of multiple transceivers portion of an EM measurement system suitable for use in various embodiments of the present teachings.

The present disclosure provides systems and methods for performing electromagnetic tomography and electromagnetic tomographic angiography, which can address various limitations of conventional electromagnetic tomography, such as those discussed above. In some embodiments, the present teachings provide systems and methods for dynamic, on-line electromagnetic tomographic angiography.

Various terms are used herein in accordance with their ordinary meanings in the art. The term "about," as used herein, denotes a variation of at most 10% around a numerical value. For example, about 100 μm means in the range of 90 μm-110 μm. The term "substantially," as used herein, denotes a deviation, if any, from a complete state and/or condition of at most 10%.

Some examples of applications of angiographic systems and methods of this disclosure are illustrated here in connection with monitoring of cardiac activity and diagnosis of cardiovascular diseases (CVD). Cardiovascular Diseases (CVDs) are number one killer in the world, meaning more people die annually from CVDs than from any other cause. Most CVDs can be prevented, and early diagnosis and treatment are critical. Technological revolutions in application of wearable technologies for personalized medicine will open up new horizons in prevention and treatment of CVDs with valuable contributions to overall societal health and wellbeing.

It should, however, be understood that the present teachings are not limited to monitoring of cardiac activity and diagnosis of CVDs. Rather, it will readily be understood by one having ordinary skill in the relevant art ("Ordinary Artisan") as informed by the present teachings that the present disclosure has broad utility and applications. Many embodiments, such as adaptations, variations, modifications, and equivalent arrangements, will be disclosed by the embodiments described herein and fall within the scope of the present disclosure.

Accordingly, while the present disclosure provides details in relation to one or more embodiments, it is to be understood that this disclosure is illustrative and exemplary. The detailed disclosure herein of one or more embodiments is not intended, nor is to be construed, to limit the scope of patent protection afforded by the present disclosure, which scope is to be defined by the claims and the equivalents thereof.

Thus, for example, any sequence(s) and/or temporal order of steps of various processes or methods that are described herein are illustrative and not restrictive. Accordingly, it should be understood that although steps of various processes or methods may be shown and described as being in a sequence or temporal order, the steps of any such processes or methods are not limited to being carried out in any particular sequence or order, absent an indication otherwise Indeed, the steps in such processes or methods generally may be carried out in different sequences and orders while still falling within the scope of the present disclosure.

Within non-ionizing portion of the electromagnetic spectrum, any dielectric object, including biological objects, can be differentiated and hence be imaged based on their dielectric properties. From non-biomedical area, e.g., in oil-water-salt suspensions (including crude oil mixtures), the dielectric properties of oil are significantly different from those of water or salted water (e.g., the dielectric permittivity of oil is generally less than the respective dielectric permittivity of water or salted water), thus creating a favorable environment for imaging. In the biomedical domain, the dielectric properties of tissues with a high water content (e.g., muscle) are significantly different than the dielectric properties of tissues with a low water content (e.g., fat, bone, etc.). Changes in dielectric properties of tissues caused by various physiological and pathological alterations, such as blood content, ischemia, infarction, hypoxia and malignancy have been intensively studied. For example, the dielectric properties of brain soft tissues and skeletal muscles tissues are sensitive to its blood content and dielectric properties of myocardium are sensitive to its blood content and hypoxia with almost immediate effect following intervention. Furthermore, the spectral changes in dielectric properties of tissue caused by acute blood deficiency and acute hypoxia are different. And the changes in dielectric properties of biological tissues have time dependence, allowing potential diagnosis of viability of tissues, the time development of tissue damage and/or an assessment of an efficacy of treatment.

The present disclosure generally relates to systems and methods for electromagnetic tomographic imaging of any dielectric object, such as electromagnetic tomography of biological objects or part of biological object (for example, a human head or human limb) and electromagnetic tomographic angiography of blood vessels of biological objects. Electromagnetic tomographic imaging can be applied to imaging of non-metal objects, such as, but not limited to, biological objects, including imaging of parts of human body, such as cerebral or cardiac or musculoskeletal imaging or can be applied to industrial applications, such as imaging of crude oil in oil pipes or can be applied to imaging and assessment of a composition of oil-water-salt suspensions in desalters of oil refineries or can be applied to imaging and assessment of oil-refined products in refinery columns. Particular applications of electromagnetic tomographic angiography discussed and presented herein include monitoring of cardiac activity and/or diagnosis of cardiovascular diseases (CVDs), e.g., via cardiac angiography as well as for a cerebral tomographic angiography. However, the systems and methods disclosed herein are not limited to a particular biomedical field of use. The methods and systems of the present teachings for electromagnetic tomographic angiography are applicable to other biomedical areas, such as extremities angiography, etc.

With reference to the flow chart of FIG. 1A, a method according to an embodiment for imaging of a dielectric object can include irradiating at least a portion of the object with radiation having a frequency in a range of about 0.01 GHz to about 10 GHz during a first time interval, wherein the frequency corresponds to a wavelength of the radiation within the object that is greater than at least one dimensional size of the object and/or a dielectric inhomogeneity of interest inside the object to be imaged. At least a portion of a radiation that is transmitted through the object and/or reflected and/or scattered from the object in response to the illuminating radiation can be detected, e.g., at a plurality of spatial locations around the object, to generate a first dataset. In a second time interval, at least a portion of the object (e.g., the same portion illuminated during the first time interval) is irradiated with radiation having a frequency in a range of about 0.01 GHz to about 10 GHz, wherein the frequency corresponds to a wavelength of the radiation within the object that is greater than at least one dimensional size of the object and/or a dielectric inhomogeneity of interest inside the object to be imaged. The frequency of the radiation employed for illuminating the object in the second time interval can be the same as or different from the frequency of the radiation employed for illuminating the object in the first time interval. As noted above, in cases where different radiation frequencies are employed, the dispersion property of the object under study should be taken into account in constructing a dielectric image of the object.

At least a portion of radiation that is transmitted through the object and/or reflected and/or scattered from the object is detected, e.g., at a plurality of spatial locations around the object to generate a second dataset. A third dataset can be generated based on the first and the second dataset, e.g., as a combination or functional of the first and the second dataset. By way of example, in some embodiments, the third dataset can correspond to the $1^{st}$ or $2^{nd}$ dataset plus a weighted normalized difference between the respective data points of the first and the second datasets. A digital data processor can be used to reconstruct an image of one or more dielectric properties of the object (or a portion thereof), e.g., the real and/or imaginary parts of the dielectric property, based on the third dataset. In some embodiments, the reconstructed image can exhibit a sufficient spatial resolution to allow detection of a dielectric inhomogeneity of interest within the object, which can have at least one-dimensional size less than the wavelength of the radiation within the object.

In some cases, the first and the second datasets can be obtained when the object is in a first and a second state in which the object exhibits different dielectric properties. Such differences in the dielectric properties, though small in some cases, can be sufficient to allow obtaining a dielectric image of the object based on the third dataset with a desired (target) resolution, e.g., a resolution of better than about 2 mm.

By way of example, multiple datasets can be acquired such that the datasets are linked to periodically changing conditions of the object (e.g., multiple datasets within a single or multiple cardiac cycles can be acquired, e.g., such that one or more datasets correspond to diastolic phase of the cardiac cycle and one or more datasets correspond to the systolic phase of the cardiac cycle). A dataset generated based on these multiple datasets (herein referred to as a resultant or a composite dataset) can be used to reconstruct a dielectric image of the object.

In some embodiments, the acquisition of data in two or more datasets can be synchronized with a particular state of the object under study. For example, the acquisition of data in one dataset can be synchronized with the diastolic phase of the cardiac cycle and the acquisition of data in another dataset can be synchronized with the systolic phase of the cardiac cycle. By way of example, and without limitation, a subject's electrocardiogram of a subject's can be utilized for such synchronization. In other cases, the variation of blood pressure can be utilized for such synchronization. In general, in some embodiments, any suitable physiological parameter may be employed for synchronizing the acquisition of data with a particular dielectric state of an object. Referring now to FIG. 1B, a system 100 for generating a dielectric image of a dielectric object according to an embodiment of the present teachings includes a data acquisition subsystem 102 operating under the control of a controller 104, where the data acquisition subsystem can be utilized to illuminate a target object with radiation having a frequency in a range of about 0.01 GHz to about 10 GHz and to detect radiation transmitted through the object and/or reflected and/or scattered by the object.

Figure 2A:
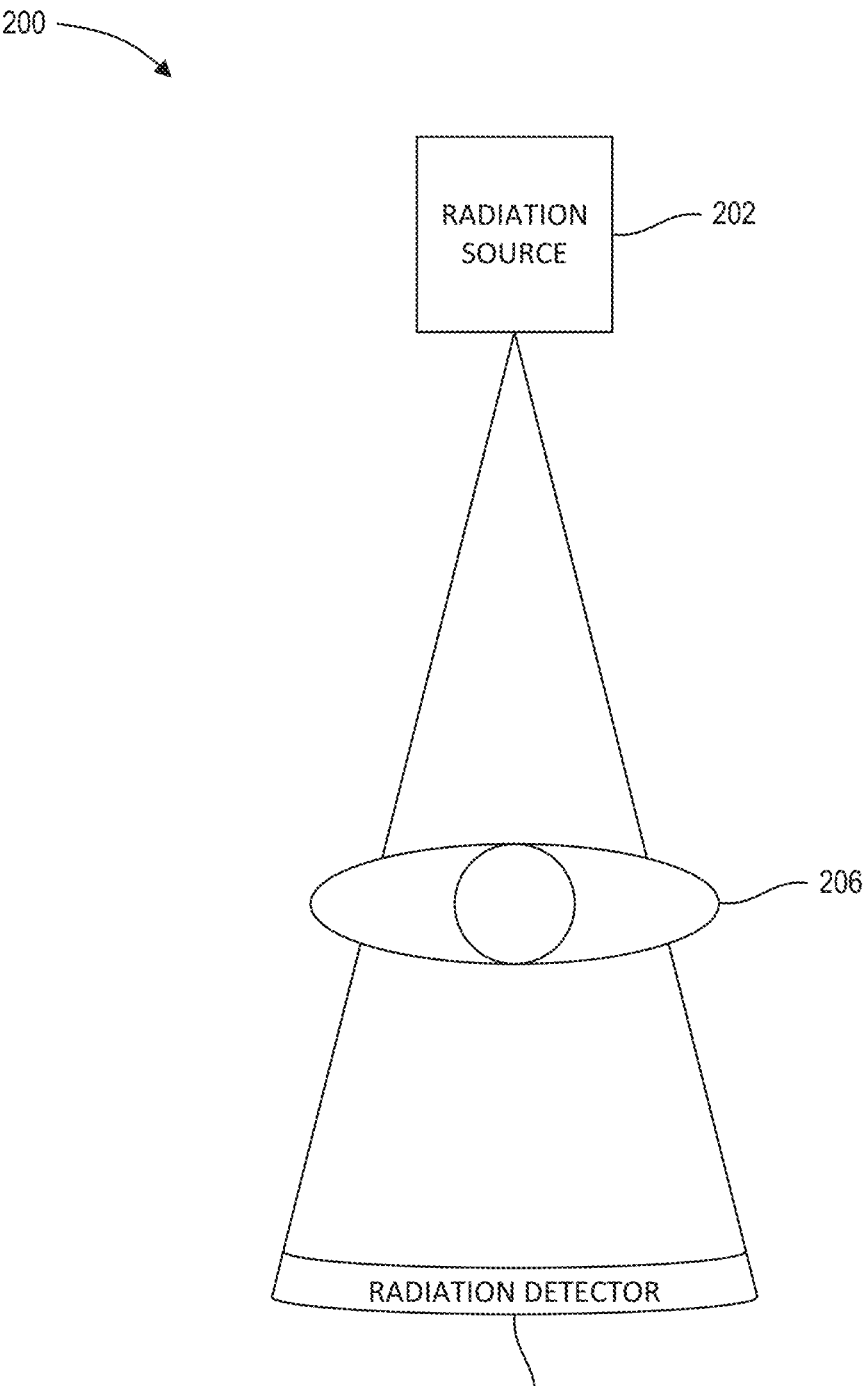
Figure 2B:
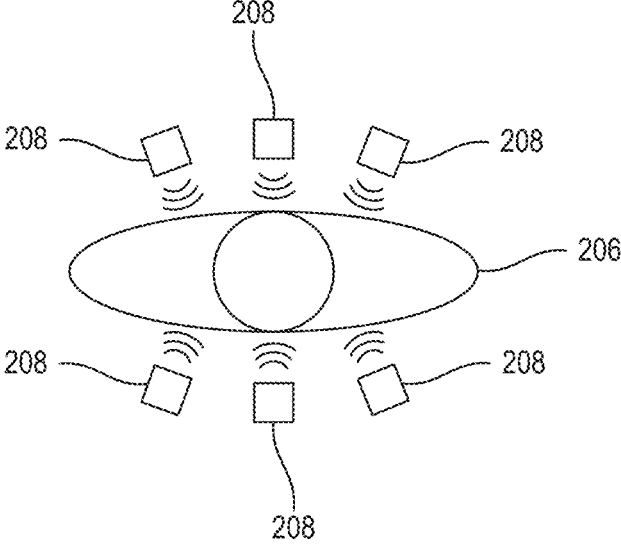

By way of example, FIG. 2A schematically depicts a simplified one transmitter-to-one receiver example of such a data acquisition subsystem that includes a radiation source 202 that emits radiation with a frequency in a range of about 0.01 to about 10 GHz for illuminating an object of interest 206 disposed within an examination region. The data acquisition subsystem can further include a radiation receiver 204 that detects a portion of the illuminating radiation that is transmitted through the illuminated object and provide detection signal(s) that can form a dataset (e.g., an image dataset). While FIG. 2A depicts the radiation detector 204 as being opposite the radiation source 202, in other embodiments (FIG. 2B), the radiation source 202 and the radiation detector 204 may be integrated into a plurality of transceivers 208 that are placed in contact with or in proximity of the object of interest 206. In these embodiments, the radiation sources 202 of the transceivers 208 emit electromagnetic radiation (e.g., at a frequency in a range of about 0.01 GHz to about 10 GHz) that can be directed to the object of interest 206. At least a portion of the radiation transmitted through the object and/or reflected and/or scattered by the illuminated object in response to the illuminating radiation can be detected by the detector of one or more of the transceivers.

In some embodiments, the controller can control the transceivers so as to selectively activate the transceivers for emission and detection of radiation. For example, a dataset can be generated by detecting, for each transceiver emitting radiation, the radiation that is detected by one or more of the other transceivers. The data can be compiled as a matrix where each matrix element corresponds to an emission-detection relationship between pairs of the transceivers.

Referring again to FIG. 1B, the system 100 further includes a data processing and analysis module 106 that can receive the data acquired by the data acquisition subsystem 102. The data processing/analysis module 106 can process multiple datasets acquired from the object, e.g., datasets acquired for different states of the object, in accordance with various embodiments of the present teachings to reconstruct a dielectric image of the object.

As noted above, in some embodiments, the controller 104, which can be in the form of a computer system that is connected to and in communication with the data acquisition subsystem and can be configured to control operation of the data acquisition subsystem. For example, in some embodiments, the controller can control the operation of a plurality of transceivers, e.g., to selectively activate them for emission and detection of the radiation.

In some embodiments, the system 100 can further include a synchronization signal generator 108 in communication with the controller 106 to provide synchronization signals to the controller 106. By way of example, in some embodiments, the synchronization signals can be based on variation of a physiological parameter of interest, e.g., various phases of a cardiac cycle. In this embodiment, the system 100 further includes a physiological measurement system 110, e.g., an electrocardiography device or a blood pressure measurement device. By way of example, and without limitation, in some embodiments wherein the system 100 is employed to image one or more blood vessels, the controller 104 may be configured to utilize an electrocardiogram to synchronize operation of the data acquisition subsystem 102 with certain phases of the cardiac cycle, e.g., the diastolic or the systolic phase.

While FIG. 1 depicts the controller 104 and the data processing and analysis module (herein also referred to as an analyzer) 106 as separate units, in other embodiments, the controller 104 and the analyzer 106 may be integrated into the same computer system. As discussed in more detail below, analyzer 106 can include an image reconstructor that employs algorithm(s) (e.g., the algorithms discussed herein) to process the image data generated by the data acquisition subsystem to reconstruct a dielectric image of the object of interest 206 and outputs the image(s) to a display. In some embodiments, the analyzer 106 employes further algorithms to analyze information in the images to arrive at a medical diagnosis (e.g., partial of full occlusion of blood vessels, tissue hypoxia, ischemia or infarction, stroke (both ischemic and hemorrhagic), compartmental injury, tissue malignancies).

By way of example, in cases in which two phases of data acquisition are employed (the method can be readily generalized to more than two phases of data acquisition), using the electromagnetic data during one phase of interest (herein referred to without lack of generality as phase No. 1), a matrix of complex EM fields (for example: amplitude and phase) from N transceivers measured on M receivers is formed and calibrated (M*N matrix), where the matrix elements are denoted herein as $Sij^{EXP-1}$, i=1, N; j=1, M; using raw data acquired from electromagnetic measurements system during another phase of interest (herein referred to without loss of generality as phase No. 2) a matrix of complex EM fields (for example: amplitude and phase) from N transceivers measured on M receivers (M*N matrix)–$Sij^{EXP-2}$, i=1, N; j=1, M; ix) is formed and calibrated to generate an M*N matrix of calibrated $Sij^{EXP-2}$ phase 2 experimental data. A perturbated M*N matrix with matrix elements $Sij^{EXP1/2}$ is calculated as follows: $Sij^{EXP1/2}=Sij^{EXP-1}+\alpha(Sij^{EXP-1}-Sij^{EXP-2})/|Sij^{EXP-1}|$, where $|Sij^{EXP-1}|$ is a norm of complex $Sij^{EXP-1}$ and α—is a parameter chosen by a trial method or in the form of $Sij^{EXP\ 1/2}=Sij^{EXP-1}+\beta(Sij^{EXP-2}-Sij^{EXP-1})/|Sij^{EXP-2}|$, where $|Sij^{EXP-2}|$ is a norm of complex $Sij^{EXP-2}$ and β— is a parameter chosen by a trial method OR in another forms of linear combination of $Sij^{EXP-1}$, $Sij^{EXP-2}$, $|Sij^{EXP-1}|$, $|Sij^{EXP-2}|$, and weighting parameter α. In case when more than two datasets used (for example, K datasets), the perturbated M*N matrix is calculated as a linear combination of all or portions of K elements $Sij^{EXP-m}$ their norms $|Sij^{EXP-n}|$ and weighting parameters an (m=1,K; n=1,K−1).

Further, the analyzer 106 is configured to apply an iterative method to the perturbated matrix to reconstruct an image as follows: using an "initial guess" as an initial distribution of dielectric properties $\varepsilon_1(r)$ at $1^{st}$ iteration (for example, but not limited to, a homogeneous distribution of dielectric property $\varepsilon_1(r)=\varepsilon_0$, where $\varepsilon_0$ is, for example, but not limited to, a known dielectric properties of outside of an object under study, but inside of an imaging domain); calculating of electromagnetic (EM) fields distribution from N (i=1, N) transceivers within the study domain $E_i(\varepsilon_k(r))$ and on M (j=1, M) receivers $Sij^{THR}$ at $k^{th}$ iteration (k=1,K); calculating a change in dielectric properties $\Delta(\varepsilon(r))$ using gradient or/and Newton type of methods in form of: a) gradient $\Delta(\varepsilon(r))\sim\Sigma_{i,j}^{N,M}E_i^*(\varepsilon_k(r)\times E_j^*(\varepsilon_k)\times(Sij^{THR}-Sij^{EXP}_{1/2}$ b) for Newton $\Delta(\varepsilon(r)\sim$inversion of matrix $D_{ij}=(E_i(\varepsilon_k(r))\times E_j(\varepsilon_k(r))$; updating the distribution of dielectric properties within the study domain at iteration k as $\varepsilon(r)_{updated}=\varepsilon_{k-1}(r)+\Delta(\varepsilon(r))$—this is an updated angio-dielectric image; making decision: if $\varepsilon(r)_{updated}$ satisfies decision making criteria, then stopping the iterative images reconstruction procedure, taking the reconstructed angio-dielectric image $\varepsilon(r)_{updated}$ to either end-users or to further post-processing and analysis and store reconstructed image in memory; making decision: if $\varepsilon(r)_{updated}$ does not satisfy decision making criteria, then taking the reconstructed angio-dielectric image $\varepsilon(r)_{updated}$ to the next iteration cycle; making multiple reconstructed images over time (for example, but not limited to synchronized with ECG), so the images might be used as frames to compile a movie (optional); providing that decision making means is based on the satisfaction of the following (for example, but not limited to) at iteration k: $\Sigma_{i,j}^{N,M}|(Sij^{THR\_iter=k}-Sij^{EXP1/2})|<\beta*\Sigma_{i,j}^{N,M}|(Sij^{THR\_iter=1}-Sij^{EXP1/2})|$, where |A| denotes a norm of complex A and $\beta$ is a convergence accuracy parameter, for example, but not limited to a value in a range of about 0.9 to about 0.99, e.g., 0.95. The analyzer 104 can optionally store the electromagnetic measurements data, cardiac activity data (for example, but not limited to ECG data) and reconstructed dielectric image, e.g., angio-dielectric images $\varepsilon(r)_{updated}$, in a database 112, which can be a memory module within the analyzer 104 or a separate database. In the latter case, the analyzer can utilize a variety of communications protocols to communicate with the database.

Figure 3:
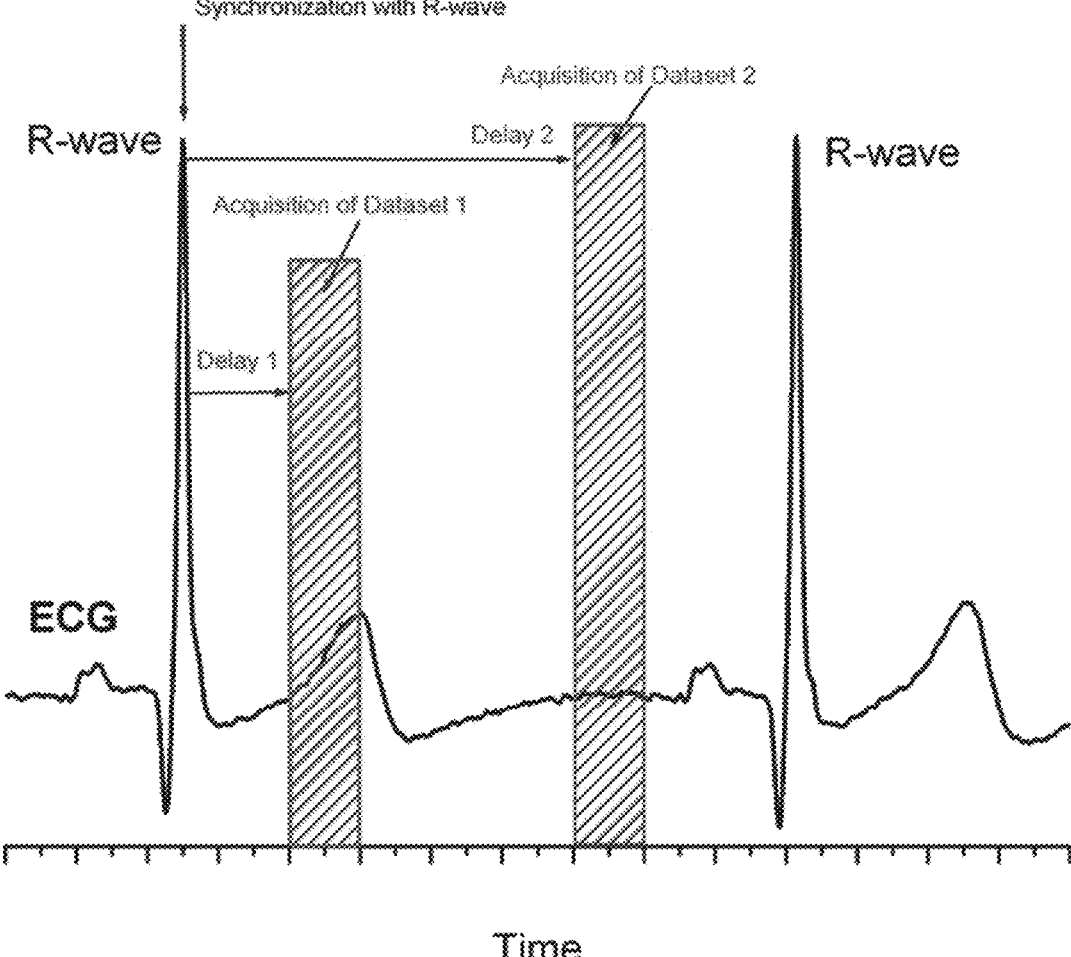
FIG. 3 shows a schematic of electrical signals associated with a cardiac cycle depicting a diastolic phase and a systolic phase of the cardiac cycle, FIG. 4 schematically depicts a system according to an embodiment of the present teachings.

As noted above, in some embodiments, the physiological measurements relate to different phases of the cardiac cycle. For example, the physiological measurement device 110 can be an electrocardiogram (ECG) device. With reference to FIG. 3, in some such embodiments, the acquisition of multiple datasets, e.g., two datasets in this example, within a cardiac cycle can be synchronized with the various phases of the cardiac activity. For example, as shown in FIG. 3, the acquisition of one dataset can be synchronized with the diastolic phase of the cardiac cycle and the acquisition of the other dataset can be synchronized with the systolic phase of the cardiac cycle. For example, the R-wave of an electrocardiogram can be utilized as a trigger signal indicating the start of a new cardiac cycle. The trigger signal can be transmitted to a controller (such as the controller 106 depicted in FIG. 1B) and the controller can be configured to begin the acquisition of a first dataset after a first predefined time delay relative to the receipt of the trigger signal so as to synchronize the acquisition of the first dataset with the systolic phase of the cardiac cycle and to begin the acquisition of a second dataset after a second predefined delay relative to the trigger signal so as to synchronize the acquisition of the second dataset with the diastolic phase of the cardiac cycle.

Figure 4:
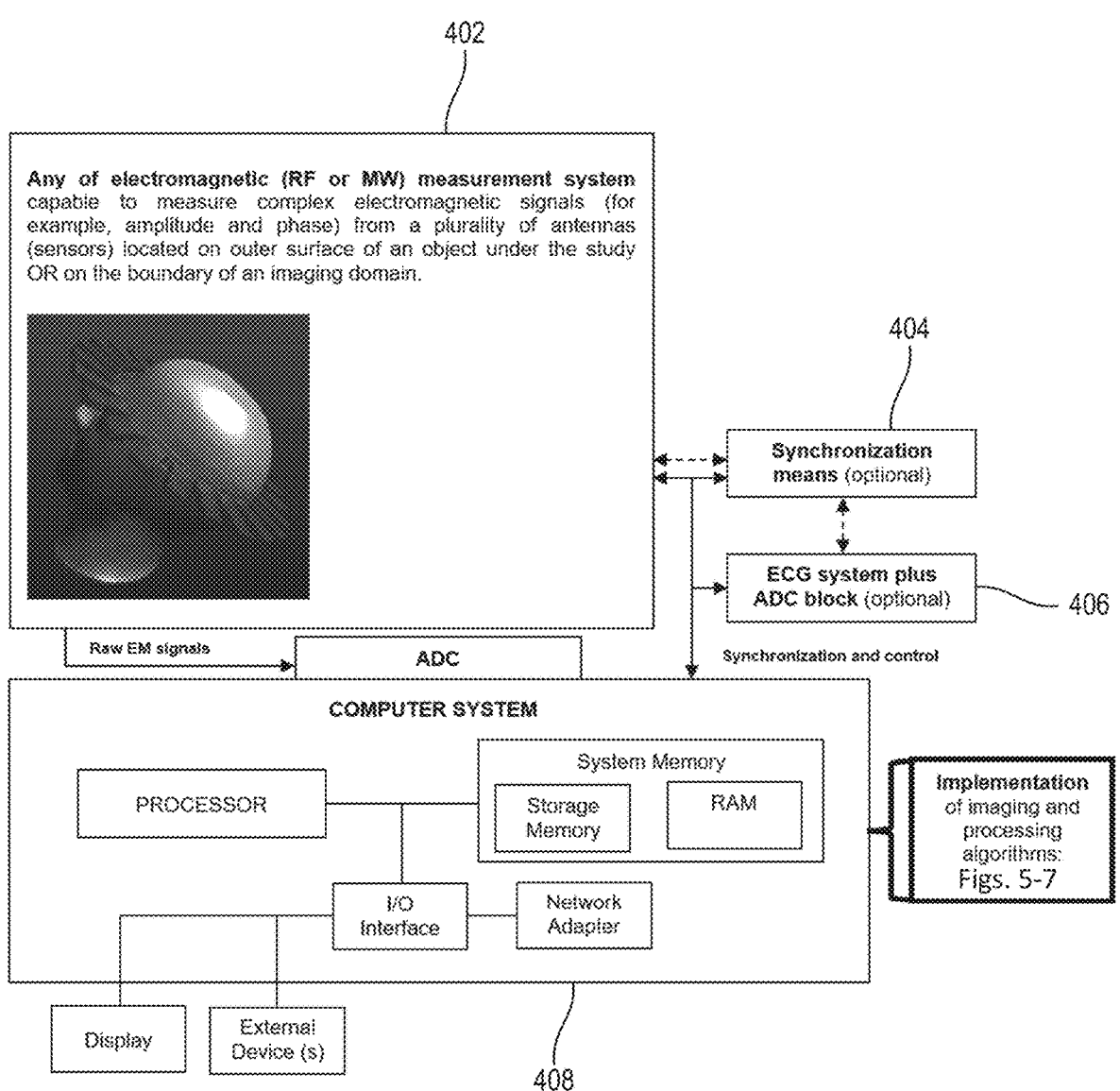

By way of example, FIG. 4 schematically depicts a block-sketch of an Electromagnetic Tomography and Tomographic Angiography (ETTA) system 400 in accordance with an exemplary embodiment. The ETTA system may serve as the system 100.

The exemplary system 400 includes an EM measurement system 402 that can generate complex-valued data (including particular case of real-valued data, when an imaginary part is equal to zero, referring to the case when only one component of EM field, for example—amplitude, is measured) based on detection of radiation that is transmitted through the object, and/or reflected and/or scattered by an object (e.g., a biological component of the human heart) in response to illumination. In this example, a synchronization device (e.g., a controller) 404 can receive synchronization signals from an ECG system and can use the synchronization signals to synchronize the acquisition of EM data with various phases of the cardiac cycle. For example, multiple datasets each corresponding to a particular phase of the cardiac cycle, e.g., two datasets where one of which corresponds to the systolic phase and another to the diastolic phase) can be generated.

The datasets can be digitized and calibrated, e.g., by an analog-to-digital converter (ADC) incorporated in the EM measurement system and the digitized datasets can be received by a data processing and analysis module 408 for processing and reconstruction of an electromagnetic image of the spatial region(s) of interest. In this embodiment, the data processing and analysis unit is implemented as a computer system having a processor 408, system memory including permanent storage memory as well as random access memory (RAM), and I/O interface for displaying the reconstructed images as well as communicating with external devices, e.g. keyboard, etc. A network adapter allows the data processing/analysis module to communicate, e.g., via a variety of different wired and/or wireless protocols, with other devices, such as other computer systems. The instructions for processing the EM data in accordance with present teachings can be stored in the permanent memory and can be transferred to the RAM under control of the processor during run-time to execute the methods according to various embodiments for reconstruction of the electromagnetic image in accordance with the present teachings.

Figure 5:
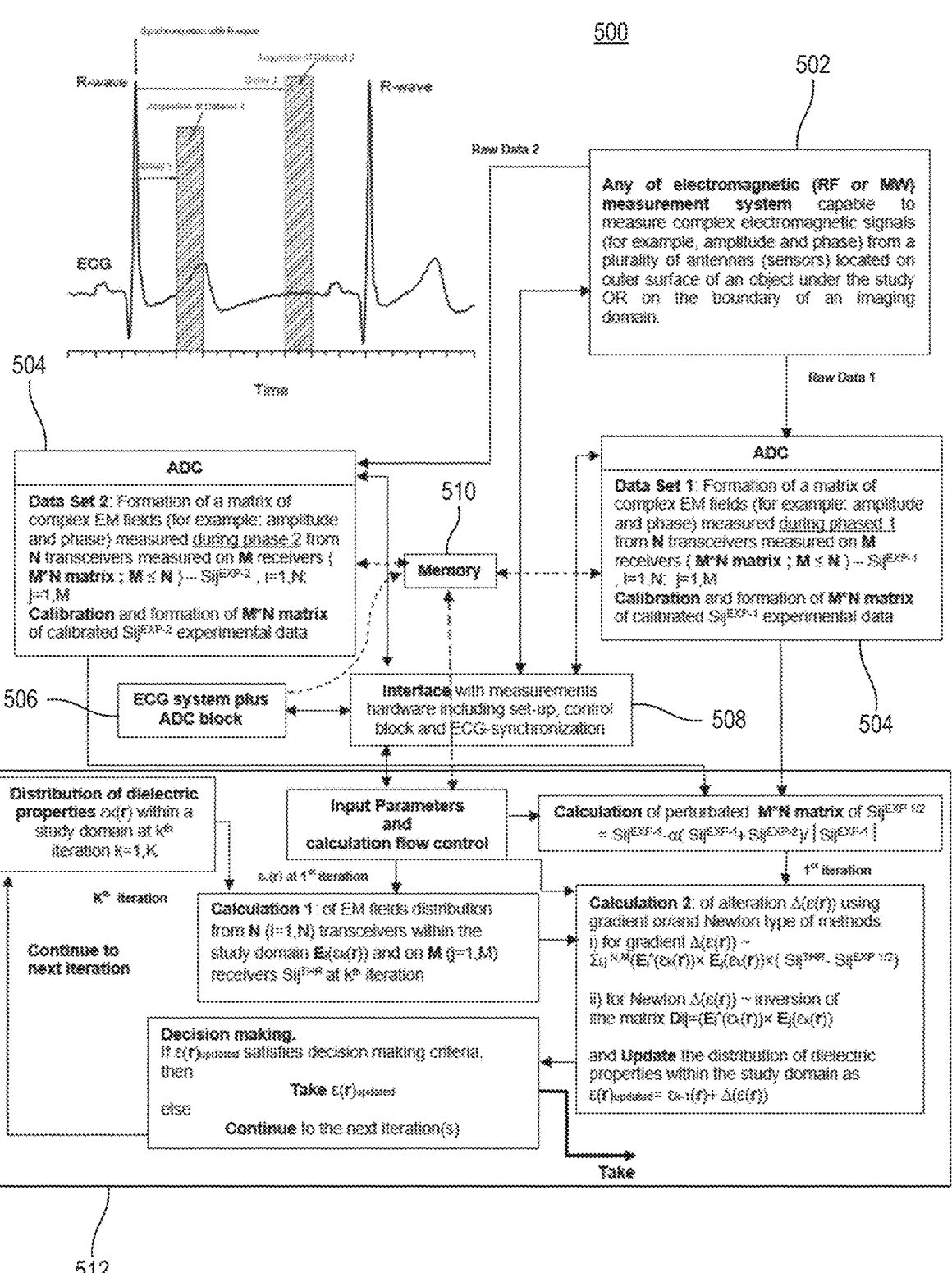
FIG. 5 is a block diagram depicting various exemplary components of an electromagnetic tomographic angiography (ETA) system 500 according to an embodiment of the present teachings

By way of further illustration and with reference to FIG. 5, a block diagram depicting various exemplary components of an electromagnetic tomographic angiography (ETA) system 500 according to an embodiment of the present teachings is shown, which is configured to generate an electromagnetic image of a target of interest, e.g., an blood vessel, in the human brain. The ETA system 500 includes an electromagnetic (e.g., RF or MW) system 502 that can provide complex-valued electromagnetic signals (e.g., amplitude and phase) (including particular case of real-valued data, when an imaginary part is equal to zero, referring to the case when only one component of EM field, for example—amplitude, is measured) using, e.g., a plurality of sensors (e.g., antennas) located on an outer surface of an object under study and/or on the boundary of an imaging domain, or within the object. An analog-to-digital converter (ADC) 504, which can be, e.g., incorporated in the electromagnetic system, can receive and digitize the electromagnetic signals.

A cardiac-activity measurement device 506 (ECG system and ADC block) can generate ECG signals and send digitized versions of those signals to a control interface 508, which can in turn generate synchronization signals based on the ECG signals for transmission to the EM measurement system 502. In this example, in response to the synchronization signals, the EM measurement system 502 generates two digitized datasets, where one of the datasets, e.g., dataset 1, contains EM signals associated with one phase (e.g., the systolic phase) of the cardiac activity and the other dataset, e.g., dataset 2, contains EM signals associated with the other phase (e.g., the diastolic phase) of the cardiac activity. In some embodiments, rather than synchronizing the acquisition of data in real time with phases of cardiac activity, a memory module 510 can receive and store the time-stamped ECG signals (herein also referred to as time-flagged ECG signals) and the controller can use time flags associated with the cardiac data to synchronize the datasets with the respective phases of the cardiac activity and store the synchronized datasets.

A data processing, image reconstruction and analysis module 512 can receive the two datasets and can process the datasets to reconstruct a dielectric image of the target region of the subject's brain, e.g., an artery. In this example, the controller can provide the input parameters for initiation of reconstruction of the electromagnetic image to the module 512, e.g., the dielectric properties for use in the first iteration of the calculations.

A perturbated matrix having the following matrix elements, for example but not limited to $Sij^{EXP^{1/2}}=Sij^{EXP-1}+$ $\alpha(\text{Sij}^{EXP-1}-\text{Sij}^{EXP-2})/|\text{Sij}^{EXP-1}|$, where $|\text{Sij}^{EXP-1}|$ is a norm of complex $\text{Sij}^{EXP-1}$ and $\alpha$— is a parameter chosen by a trial method, can be constructed based on the two acquired datasets.

Figure 6A:
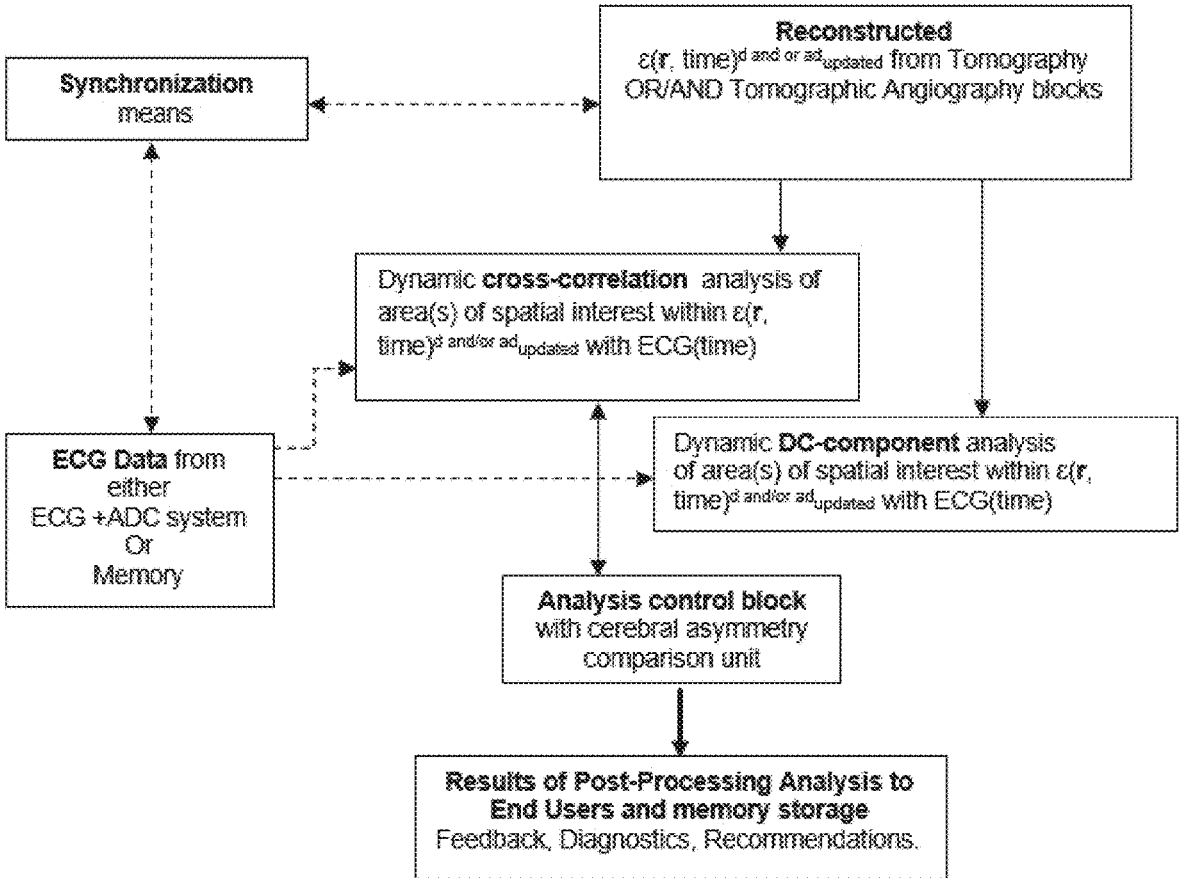
FIG. 6A is a block diagram depicting various steps of a method according to an embodiment for post-processing a dielectric image generated according to the present teachings for assessment of oxygenation in tissue.

In some embodiments, the electromagnetic image can be subjected to post processing, e.g., to provide diagnosis, feedback, or recommendation. By way of example and with reference now to FIG. 6A, an example of such post processing of reconstructed images $\varepsilon(r)_{updated}$ for an assessment of oxygenation status and viability of biological tissue is provided. As shown in FIG. 6A, the method includes (typically in biomedical applications of the method): i) receiving one or more reconstructed dielectric images $\varepsilon(r)^d_{updated}$ and/or reconstructed angio-dielectric images $\varepsilon(r)^{ad}_{updated}$; ii) receiving cardiac data either directly from a cardiac measurement system or from memory in the form of, for example, but not limited to, digitized ECG data; iii) synchronizing a time of acquisition of raw electromagnetic data used to reconstruct images with cardiac activity from measured (for example, but not limited to) data in form of ECG recording or cardiac data with time-flags stored in memory; iv) providing a dynamic cross-correlation analysis of spatial region(s) of interest within $\varepsilon(t, \text{time})^d_{updated}$, $\varepsilon(r, \text{time})^{ad}_{updated}$ with ECG(time) by computing the following:

$$\sum\nolimits_{i=1+k}^{M+k} E_i \times (E_i - E_{mean}) \times (F_i - F_{mean})/$$

$$\left( \sqrt{\sum\nolimits_{i=1+k}^{M+k}(E_i - E_{mean})^2} \times \sqrt{\sum\nolimits_{i=1+k}^{M+k}(F_i - F_{mean})^2} \right)$$

wherein, $E_i$ denotes an $i^{th}$ reading of $\varepsilon(r, i^{th}$ time reading$)^d_{updated}$ or $\varepsilon(r, i^{th}$ time reading$)^{ad}_{updated}$ at spatial point $(x,y,z)$ of interest, $E_{mean}$ denotes a mean of $E_i$ over k-timely points at spatial point $(x,y,z)$ of interest; $F_i$ denotes an $i^{th}$ reading of digitized physiological data signal (for example, but not limited to digitized ECG signal) and $F_{mean}$ denotes a mean of the physiological data over k-time points; v) providing a dynamic DC-component analysis of spatial region(s) of interest within $\varepsilon(r, \text{time})^d$ and/or $\varepsilon(r, \text{time})^d_{updated}$ with ECG(time); vi) controlling calculation flow control features and an asymmetry comparison unit (for cerebral (two hemispheres) and musculoskeletal (two arms or two legs) applications only); vii) delivering the results of analysis to End users and store the results in memory.

Figure 6B:
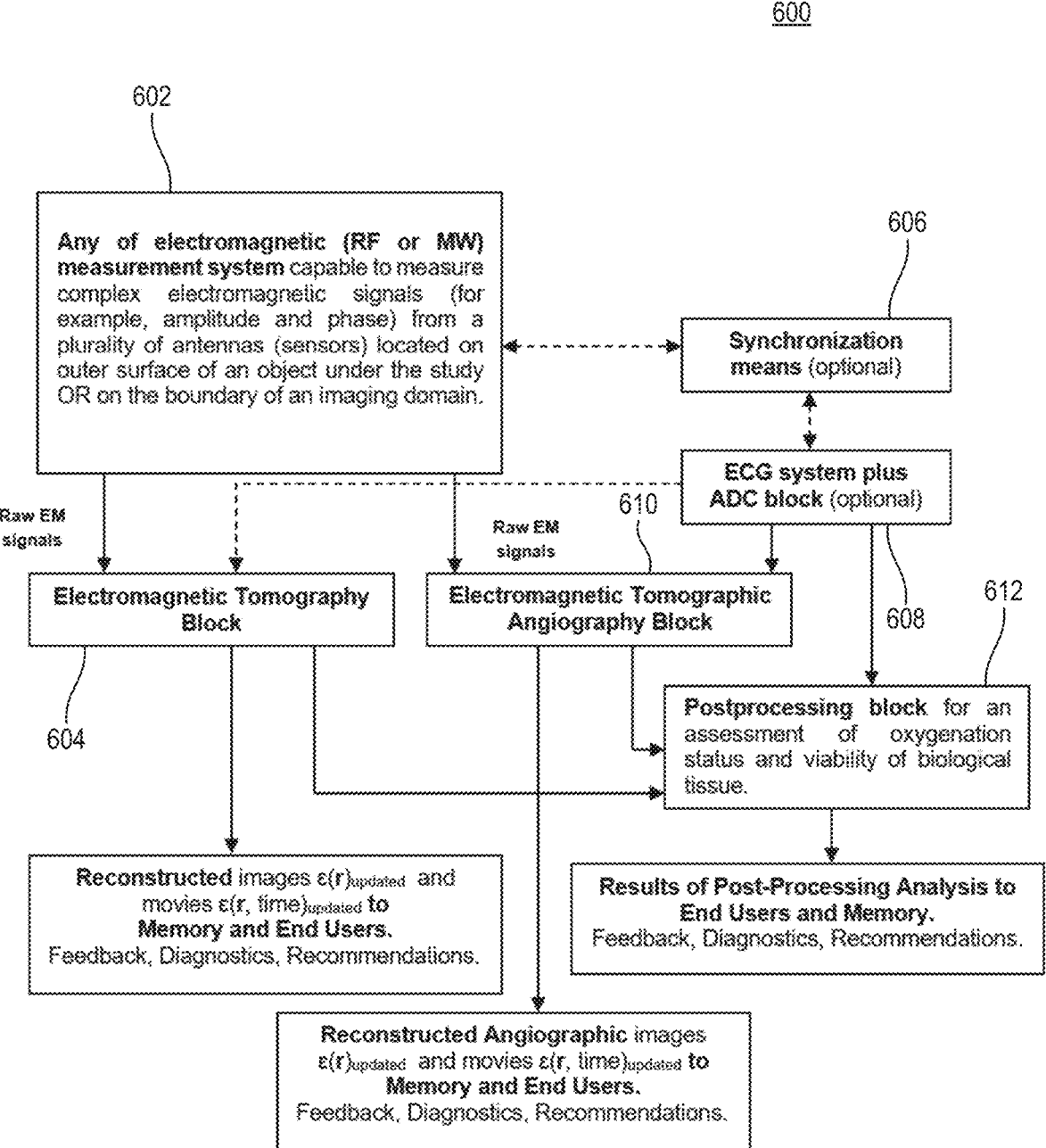
FIG. 6B is a block diagram of a system according to an embodiment for generating dielectric images and post-processing of those images.

By way of further illustration, FIG. 6B shows schematically a system 600 according to an embodiment, which includes an electromagnetic measurement system 602. The system 600 further includes an electromagnetic tomography 604 subsystem that is in communication with the electromagnetic measurement system 602 to receive the measured signals and reconstruct a dielectric image of an object under study. A synchronization module 606 that is in communication with an ECG system 608 can receive ECG data and generate synchronization signals based on the received ECG data. The synchronization signals can be employed to synchronize the collection of the EM measurement signals with different phases of the cardiac cycle, e.g., in a manner discussed above. Alternatively, the electromagnetic tomography module 604 can receive time-flagged cardiac data and can employ the time-flagged cardiac data to synchronize the received EM signals with particular phases of the cardiac cycle. Further, the system 600 further includes an electromagnetic tomographic angiography module 610 that can also receive the EM measurement signals as well as the time-flagged cardiac data. The electromagnetic tomography module 604 and the electromagnetic tomographic angiography module 610 can generate reconstructed dielectric images of the object based on the received EM data. A post-processing module 612 can process the dielectric images generated by any of the electromagnetic tomography module 604 or the electromagnetic tomography angiography module 610 in a manner described herein to assess, e.g., the oxygenation level of a tissue under study.

In some embodiments, multiple datasets can be obtained in different time intervals while the object of interest is in the same state or as the object undergoes changes in its state (e.g., conformational changes) with concomitant changes in the object's dielectric properties. In some embodiments, rather than generating a resultant/composite dataset based on the datasets generated in different time intervals, each dataset can be processed to generate a dielectric image of the object. In some cases, such images can be subjected to post processing, e.g., to monitor a particular physiological condition (e.g., oxygenation) of a subject and/or as way of detecting abnormalities in the physiological condition.

Figure 7:
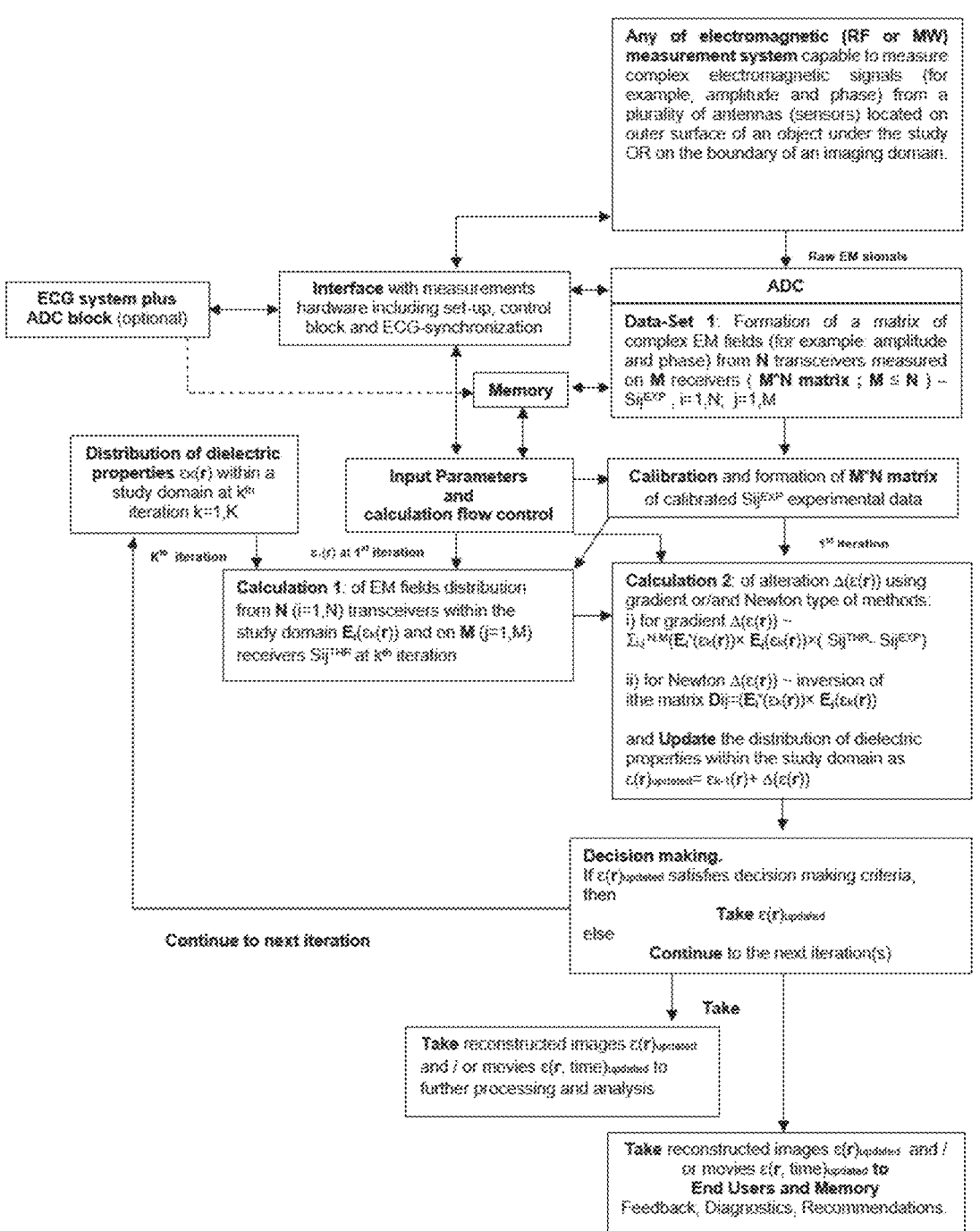
FIG. 7 is a block diagram depicting an example of an electromagnetic tomography system according to an embodiment.

By way of example, referring now to FIG. 7, a block diagram of an example of such an electromagnetic tomography (ET) method is shown in accordance with an exemplary embodiment, which includes: i) receiving complex electromagnetic signals (for example amplitude and phase) (including particular case of real-valued data, when an imaginary part is equal to zero, referring to the case when only one component of EM field, for example—amplitude, is measured) from any suitable electromagnetic (RF or microwave) measurement system capable of measuring complex electromagnetic signals, e.g., using a plurality of antennas (sensors) located on outer surface of an object under study or on the boundary of an imaging domain, ii) digitizing received complex electromagnetic signals in Analog-to-Digital converter (ADC) located, e.g., in receiving means; iii) receiving information associated with cardiac activity, for example (but not limited to), digitized ECG signals generated, for example, by the above-mentioned "ECG system plus ADC block" (typically in biomedical applications); v) synchronizing an acquisition of complex electromagnetic signals with cardiac activity from measured (for example, but not limited to) data, e.g., in the form of ECG recording generated, for example, by "ECG system plus ADC block" or cardiac data with time-flags stored in memory (typically in biomedical applications); vi) using raw data acquired from electromagnetic measurements system to form a matrix of complex EM fields (for example: amplitude and phase) from N transceivers measured on M receivers (M*N matrix)–$\text{Sij}^{EXP}$, i=1, N; j=1, M; vii) calibrating of M*N matrix of $\text{Sij}^{EXP}$ experimental data, viii) applying an iterative method to reconstruct an image as described in ix)-xv) below; ix) using an "initial guess" as an initial distribution of dielectric properties $\varepsilon_1(r)$ at $1^{st}$ iteration (for example, but not limited to, homogeneous distribution of dielectric properties $\varepsilon_1(r)=\varepsilon_0$, where $\varepsilon_0$ is, for example, but not limited to, a known dielectric properties of outside of an object under the study, but inside of an imaging domain); x) calculating electromagnetic (EM) fields distribution from N (i=1, N) transceivers within the study domain $E_i(\varepsilon_k(r))$ and on M (j==1, M) receivers $\text{Sij}^{THR}$ at $k^{th}$ iteration (k=1,K); xi) calculating alteration $\Delta(\varepsilon(r))$ using gradient and/or Newton type of methods in the form of: a) for gradient $\Delta(\varepsilon(r))\sim \Sigma_{i,j}^{N,M}(E_i*(\varepsilon_k(r))\times(\text{Sij}^{THR}-\text{Sij}^{EXP})$ b) for Newton $\Delta(\varepsilon(r))\sim$inversion of the matrix $Dij=(E_i*(\varepsilon_k(r))\times E_j(\varepsilon_k(r))$; xii) updating the distribution of dielectric properties within the study domain at iteration k as $\varepsilon(r)_{updated}=\varepsilon_{k-1}(r)+\alpha(\varepsilon(r))$—an updated image; xiii) making decision: if $\varepsilon(r)_{updated}$ satisfies predefined criteria, then stopping iterative image reconstruction procedure, presenting the reconstructed image $\varepsilon(r)_{updated}$ to end-users and/or subjecting the reconstructed image to post-processing and analysis and storing reconstructed image in memory; xiv) making decision: if $\varepsilon(r)_{updated}$ does not satisfy the predefined criteria, then the reconstructed image $\varepsilon(r)_{updated}$ can be taken to the next iteration cycle.

By way of example, in some embodiments, the predefined criteria can be based on the satisfaction of the following (for example, but not limited to) at iteration k: $\Sigma_{i,j}^{N,M}|(Sij^{THR\_iter=k}-Sij^{EXP})|<\beta*\Sigma_{i,j}^{N,M}|(Sij^{THR\_iter=1}-Sij^{EXP})|$, where |A| is a norm of complex A and $\beta$ is a convergence accuracy parameter, for example, but not limited to a value in the range of about 0.9 to about 0.99, e.g., 0.95; xiv) making multiple reconstructed images over time (for example, but limited to synchronized with ECG), so the images might be used as frames to compile a movie (optional); v) storing electromagnetic measurements data (for example, but not limited to ECG data) and reconstructed images $\varepsilon(r)_{updated}$ in memory.

Figure 8:
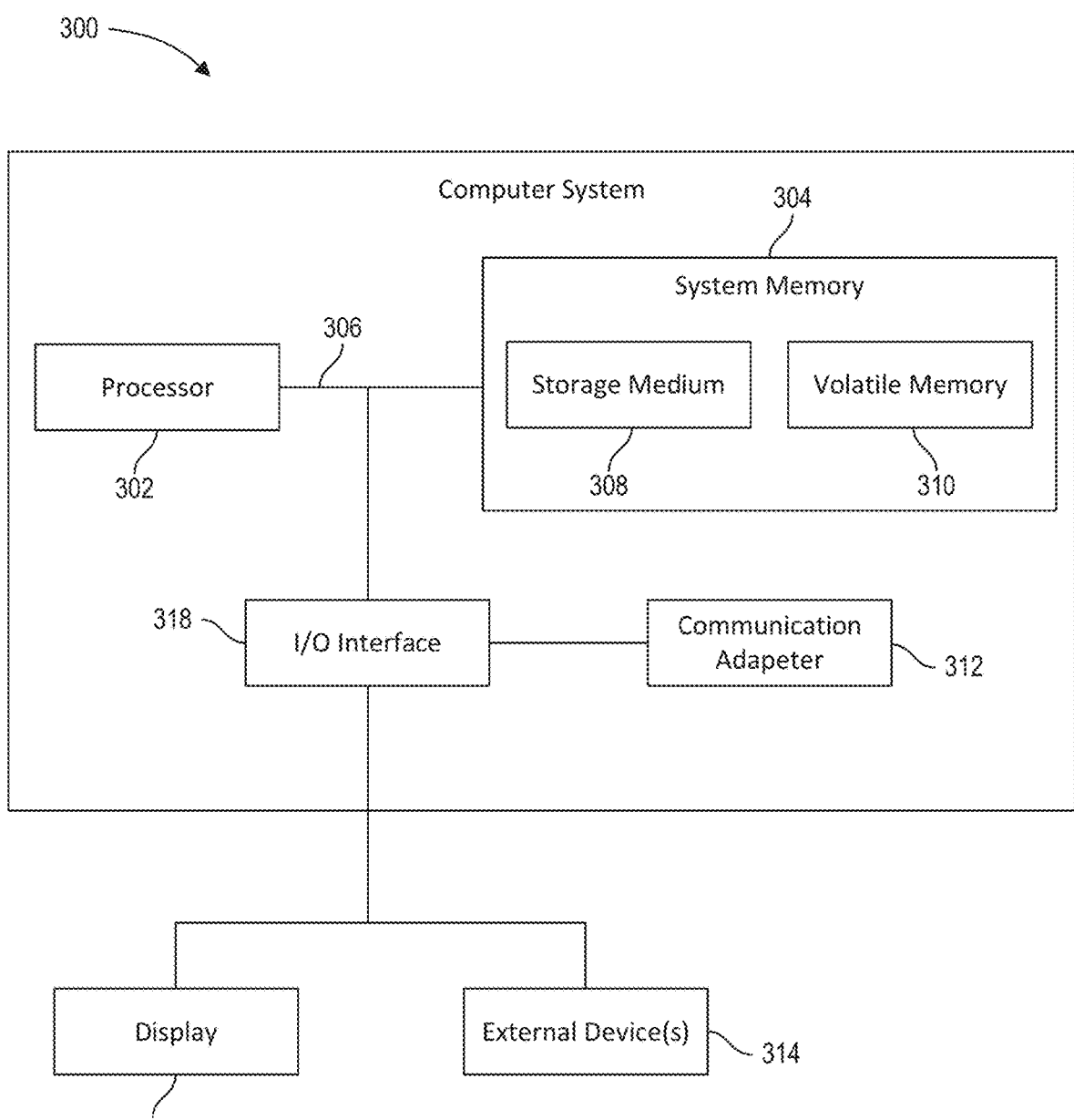
FIG. 8 schematically depicts a computer system that can be used for implementing various components of systems according to various embodiments of the present teachings.

With brief reference to FIG. 8, a computer system 300 is shown in accordance with an exemplary embodiment. The computer system 300 may serve as any computer system disclosed herein (e.g., the controller 106 and the analyzer 108). As used herein a computer system (or device) is any system/device capable of receiving, processing, and/or sending data. Computer systems include, but are not limited to, microprocessor-based systems, a system on a chip (SOC), personal computers, servers, hand-held computing devices, tablets, smartphones, multiprocessor-based systems, mainframe computer systems, and the like.

As shown in FIG. 8, the computer system 300 includes one or more processors or processing units 302, a system memory 304, and a bus 306 that couples the various components of the computer system 300 including the system memory 304 to the processor 302. The system memory 304 includes a computer readable storage medium 308 and volatile memory 310 (e.g., Random Access Memory, cache, etc.). As used herein, a computer readable storage medium includes any media that is capable of storing computer readable, program instructions and is accessible by a processor. The computer readable storage medium 308 includes non-volatile and non-transitory storage media (e.g., flash memory, read only memory (ROM), hard disk drives, etc.). Computer program instructions as described herein include program modules (e.g., routines, programs, objects, components, logic, data structures, etc.) that are executable by a processor. Furthermore, computer readable program instructions, when executed by a processor, can direct a computer system to function in a particular manner such that a computer readable storage medium comprises an article of manufacture. Specifically, the computer readable program instructions when executed by a processor can create a means for carrying out at least a portion of the steps of the methods disclosed herein.

In some embodiments, the reconstructor may be a module stored in the computer readable storage medium 308. The bus 306 may be one or more of any type of bus structure capable of transmitting data between components of the computer system 300 (e.g., a memory bus, a memory controller, a peripheral bus, an accelerated graphics port, etc.).

The computer system 300 may further include a communication adapter 312 which allows the computer system 300 to communicate with one or more other computer systems/devices via one or more communication protocols (e.g., Wi-Fi, BTLE, etc.) and in some embodiments may allow the computer system 300 to communicate with one or more other computer systems/devices over one or more networks (e.g., a local area network (LAN), a wide area network (WAN), a public network (the Internet), etc.).

In some embodiments, the computer system 300 may be connected to one or more external devices 314 and a display 316. As used herein, an external device includes any device that allows a user to interact with a computer system (e.g., mouse, keyboard, touch screen, etc.). An external device 314 and the display 316 may be in communication with the processor 302 and the system memory 304 via an Input/Output (I/O) interface 318.

The display 316 may display a graphical user interface (GUI) that may include a plurality of selectable icons and/or editable fields. A user may use an external device 314 (e.g., a mouse) to select one or more icons and/or edit one or more editable fields. Selecting an icon and/or editing a field may cause the processor 302 to execute computer readable program instructions stored in the computer readable storage medium 308. In one example, a user may use an external device 314 to interact with the computer system 300 and cause the processor 302 to execute computer readable program instructions relating to at least a portion of the steps of the methods disclosed herein. In some embodiment, the reconstructor outputs the reconstructed image to the display 316.

The following examples are provided for further elucidation of various aspects of the present teachings and are not provided to indicate necessarily optimal ways of practicing the present teachings and/or optimal results that may be achieved.

Figure 9:
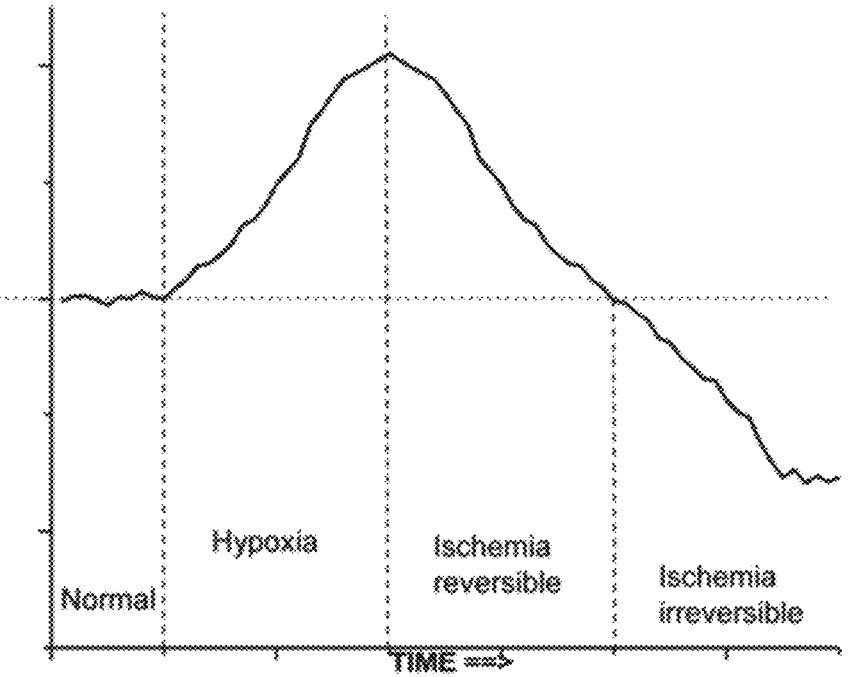
FIG. 9 illustrates a hypothetical example of tissue oxygenation from normality to tissue hypoxia to a reversible ischemic state to an irreversible ischemic change, FIGS. 10A, 10B, 10C, and 10D provide illustrations the sensitivity of the distribution of electromagnetic field within biological object to its functional/pathological conditions.

FIG. 9 is an illustrative simulated example of expected dynamics of image-to-ECG cross-correlation function of $(\varepsilon(r, time)^d_{updated}$ of $\varepsilon(r, time)^{ad}_{updated}$ with ECG(time): from normality to tissue hypoxia and further to reversable ischemic and to irreversible ischemic changes.

FIGS. 10A, 10B, 10C, and 10D provide simulated illustrations of the sensitivity of the distribution of electromagnetic field within a biological object to its functional/pathological conditions. An example of virtual dielectric model of human brain ($\varepsilon(r)$ in present teaching) with one hemisphere being normal and another one being hypoxic (FIG. 10A) is used. The arrow indicates the position of the transmitter. The family of illustrations represents from 10B to 10D: a distribution of electromagnetic field ($E_{j=1}(\varepsilon(r)$ in present teaching) within virtual dielectric model of human head ($\varepsilon(r)$ in present teaching); 10B—a distribution of electromagnetic field (amplitude) within a study domain for normal case (both hemispheres) from a source, located at arrow in 10A, 10C—a distribution of electromagnetic field (amplitude) within a study domain for the case presented in 1 (bottom hemisphere is normal, top hemisphere is hypoxic) from a source, located at arrow in 10A; 10D—the differences in amplitude of electromagnetic fields between normal case (10B) and the case in which one hemisphere is hypoxic (10C). As can be appreciated from FIG. 10D, the distribution of electromagnetic field within a virtual dielectric model of human head is sensitive to a hypoxia event in one hemisphere, providing a functional diagnostic tool to the methods of electromagnetic tomographic imaging presented in the present teachings. Such successive tomographic imaging of the presented case is provided in FIG. 11.

Figures 10A, 10B, 10C, 10D:
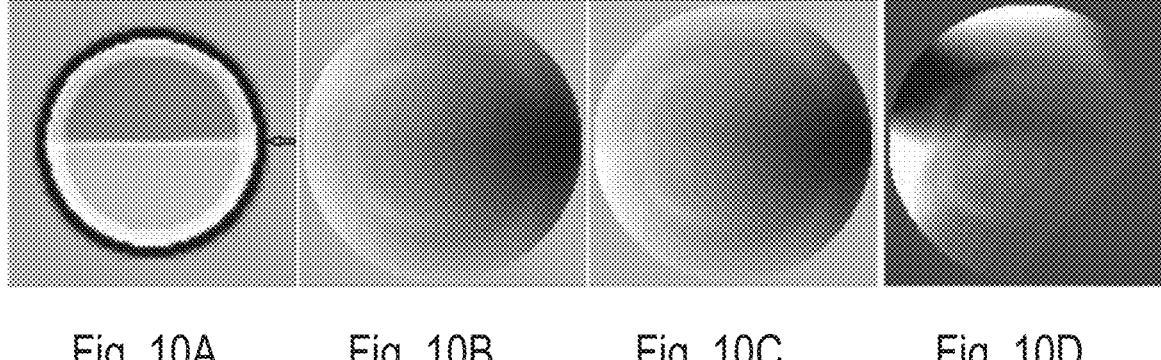

It can be appreciated from FIG. 10D that the distribution of EM field can be far more complex than just simple differences in EM fields within one hemisphere (normal) as compared with another one (hypoxic). When EM fields of frequencies at RF to MW regions, e.g., in a range of about 0.01 GHz to about 10 GHz, are used, the wavelength of EM field in biological media is comparable with the dimensions and particulars of a study domain (human head). Hence electromagnetic phenomena such as diffraction and interference play important roles. As discussed herein, the present teachings can address such shortcomings of conventional electromagnetic imaging techniques.

Figures 11A, 11B:
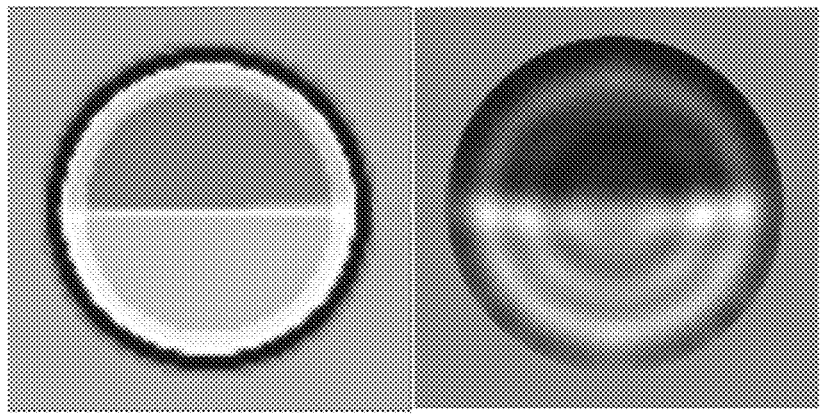
FIG. 11B illustrates a successive application of an electromagnetic tomography method (presented in this disclosure) to reconstruct an image of a virtual model of human brain (FIG. 11A) when one hemisphere is hypoxic.

FIGS. 11A and 11B are illustrations of successive application of an electromagnetic tomography method (presented in this disclosure) to reconstruct an image. The reconstructed image of virtual human head is presented on right-hand illustration in FIG. 11B. This is the case when one of hemisphere is hypoxic (virtual model is presented FIG. 11A and illustrated in details in FIG. 10).

Figures 12A, 12B, 12C:
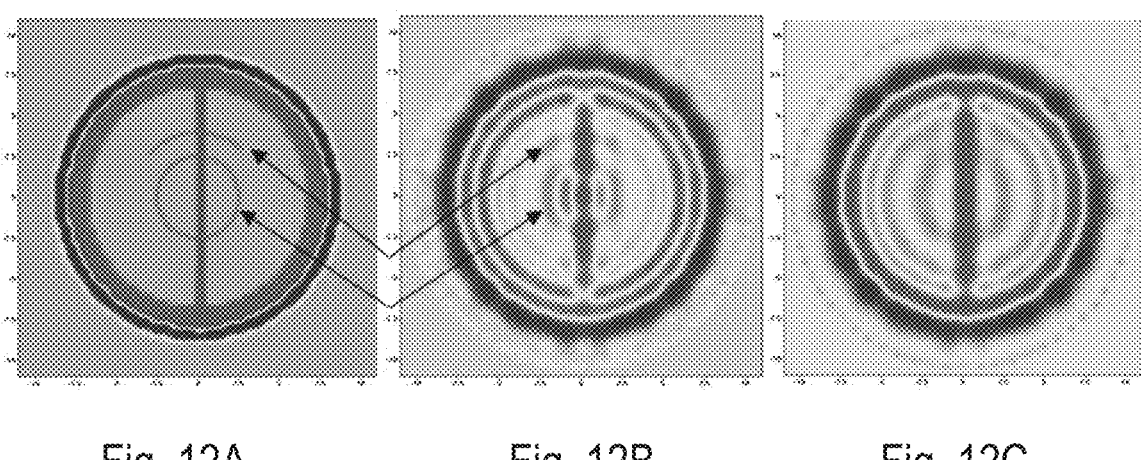
FIGS. 12A, 12B, and 12C provide illustrations of successive applications of an electromagnetic tomographic angiography method according to an embodiment of the present teachings for imaging of small vessels.

FIGS. 12A, 12B, and 12C provide illustrations of successive applications of an electromagnetic tomographic angiography method according to an embodiment of the present teachings for imaging of small vessels of diameter of about 0.86 mm. Specifically, FIG. 12A—shows XY cross-section of the virtual model of human head with vasculature. FIG. 12B is a reconstructed image of virtual human head using an embodiment of an electromagnetic tomographic angiography method according to the present teachings with parameter $\alpha$=5.0. FIG. 12C is a reconstructed image of virtual human head using standard electromagnetic tomography methods. As discussed above, electromagnetic tomography is safe and usable for functional imaging of biological objects in mobile and even wearable settings. However, conventional techniques for performing electromagnetic tomography suffer from a limited spatial resolution because of relatively large wavelength of radiation as compared with biological targets of particular interest, such as, for example blood vessels. For example, a wavelength of electromagnetic radiation at typical frequency of 1 GHz, typically used for cerebral imaging is about 4.7 cm within a brain tissue. In contrast, the systems and methods of current disclosure allow overcoming such limitations, e.g., when performing a dynamic, on-line electromagnetic tomographic angiography. The imaging results presented in FIG. 12B clearly demonstrate applicability of the method and system of this disclosure for angiography even small vessels of diameter about 0.86 mm.

FIG. 13A-13F and FIGS. 14A-14D further illustrate examples of capabilities of electromagnetic tomographic methods according to various embodiments of the present teachings for successive reconstruction of complex biological objects.

More specifically, FIG. 13A provides a map of the real part of the dielectric permittivity of a virtual model of human brain with blood vessels (including the circle of Willes). Typical diameter of a vessel was about 1.5-2.0 mm. FIG. 13B provides a map of the imaginary part of the dielectric permittivity of the virtual model of human head. FIGS. 13C and 13D show EMT images of the real and the imaginary parts of the dielectric permittivity of the virtual human brain that were generated using conventional EMT image reconstruction methods. No blood vessels are visible in these conventional images. In contrast, FIGS. 13E and 13F show EMT-angiography images of the real and imaginary parts dielectric permittivity of the virtual brain, which were reconstructed using embodiments of the present teachings. Blood vessels are clearly visible in the images depicted in FIGS. 13E and 13F.

By way of further illustration, FIGS. 14A and 14B show maps of the real and the imaginary parts of the dielectric permittivity for a virtual model of a human brain with a full occlusion of blood vessels (including the half circle of Willes) in one hemisphere. FIGS. 14C and 14D show EMT-Angiography images corresponding to the real and the imaginary parts of the dielectric permittivity that are reconstructed using an embodiment of the present teachings. The reconstructed images depicted in FIGS. 14C and 14D clearly show the occlusion in one of the hemispheres.

These imaging results demonstrate the capability of the methods and systems according to the present teachings for EMT angiography of vessel even those vessels having diameters in a range of about 1.5 to about 2 mm that are at least one order smaller than the wavelength of used electromagnetic radiation.

Figure 15A:
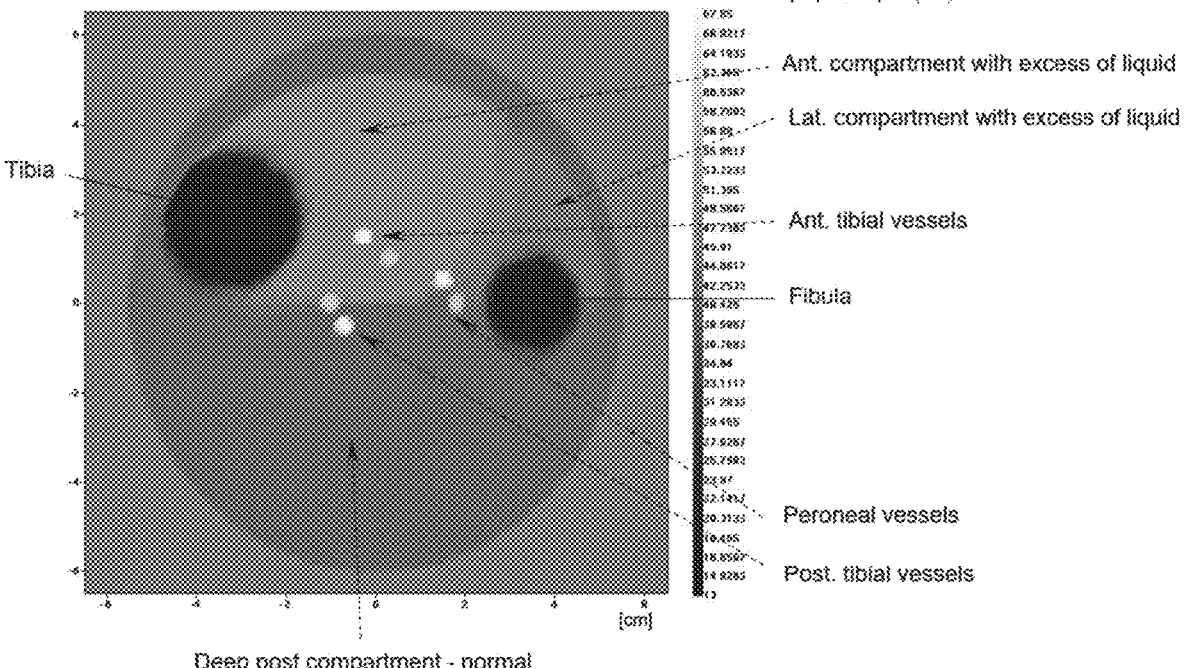
FIG. 15A shows a map of the real part of the dielectric permittivity of a virtual model of a human limb with a compartmental syndrome in Ant and Lat compartments and three group of blood vessels (each group includes both arteries and veins)

By way of further illustration, FIG. 15A shows a map of the real part of the dielectric permittivity of a virtual model of a human limb with a compartmental syndrome in Ant and Lat compartments and three group of blood vessels (each group includes both arteries and veins); FIG. 15B shows EMT-Angiography image corresponding to the real part of the dielectric permittivity that are reconstructed using an embodiment of the present teachings, clearly revealing three group of blood vessels. FIG. 15C shows differential EMT-Angiography image corresponding to the differences between i) the reconstructed image when all vessels are in function (normal vessel function—FIG. 15B) and ii) the reconstructed image when arteries are in normal function but vein are blocked (because of the rise of compartmental pressure) that are reconstructed using an embodiment of the present teachings, revealing the differences in function of all three group of vessels.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

What is claimed is:

1. A system for tomographic imaging of a dielectric object, comprising:

an electromagnetic measurement system configured to acquire electromagnetic (EM) signals and digitize the EM signals, a cardiac activity recording system configured to acquire Electrocardiogram (ECG) signals and digitize the acquired ECG signals, and a computer system with a processor configured to synchronize the EM signals and the ECG signals, reconstruct images or movies of dielectric properties of the object or reconstruct images or movies of angio-dielectric properties of the object, process the reconstructed images or movies of the dielectric properties or the angio-dielectric properties, assess hypoxia and viability of biological tissues based on the post-processed images or movies, and for images for $\varepsilon(r)^d_{updated}$ of dielectric properties or movies $\varepsilon(r, time)^d_{updated}$ of dielectric properties, the processor is further configured to:

establish parameters and geometric configuration of the EM measurement system including at least one of frequencies of the EM measurement system used, data acquisition time per acquisition frame, number of frames acquired, dielectric properties of media surrounding the object within an imaging domain, number and position of transmitting and receiving antennas of the EM measurement system, and number and position of receiving antennas of the EM measurement system, synchronize measurements of the EM signals and measurements of the ECG signals, employ raw data acquired from the EM measurement system to form a matrix EM fields from N transmitting antennas of the EM measurement system measured by M receivers of the EM measurement system according to (M*N matrix)–$\text{Sij}^{EXP}$, i=1,N; j=1,M calibrate the M*N matrix based on calibrated $\text{Sij}^{EXP}$ experimental data, iteratively reconstruct an image by using an initial homogeneous distribution of dielectric properties $\varepsilon_1(r)=\varepsilon_0$ within an imaging/study domain at the first iteration wherein $\varepsilon_0$ is a known homogeneous dielectric property of a media surrounding the object of the study or another known initial distribution of dielectric properties $\varepsilon_1(r)$ within the imaging/study domain, calculate EM field distribution from N (i=1,N) transmitters within the study domain $E_i(\varepsilon_k(r))$ on M (j=1,M) receivers $\text{Sij}^{THR}$ at $k^{th}$ iteration (k=1,K), calculate of alteration $\Delta(\varepsilon(r))$ using gradient or/and Newton type of methods in form of:

a) for gradient $\Delta(\varepsilon(r)) \sim \Sigma_{i,j}^{N,M}(E_i^*(\varepsilon_k(r)) \times \varepsilon_j^*(\varepsilon_k(r)) \times (\text{Sij}^{THR} - \text{Sij}^{EXP})$ b) for Newton $\Delta(\varepsilon(r)) \sim$ inversion of the matrix $\text{Dij}=(E_i^*(\varepsilon_k(r)) \times E_j(\varepsilon_k(r))$, update the distribution of dielectric properties within the study domain at iteration k as $\varepsilon(r)_{updated}=\varepsilon_{k-1}(r)+\Delta(\varepsilon(r))$, determine if $\varepsilon(r)_{updated}$ satisfies a decision making criteria, and in response to determining the decision making criteria is satisfied, output reconstructed image $\varepsilon(r)_{updated}$ and further process the image and store reconstructed image in a memory of the computer system, in response to determining the criteria is not satisfied, take the reconstructed image $\varepsilon(r)_{updated}$ to a next iteration cycle, wherein the criteria is based on the satisfaction of the following inequation at iteration k: $\Sigma_{i,j}^{N,M}|(\text{Sij}^{THR\_iter=k} - \text{Sij}^{EXP})| \beta^* \Sigma_{i,j}^{N,M}|(\text{Sij}^{THR\_iter=1} - \text{Sij}^{EXP})|$, where |A| is a norm of complex A and $\beta$ is a convergence accuracy parameter, provide multiple reconstructed images over time, provide input and control parameters and calculation flow control, and store electromagnetic measurements data, and cardiac activity data and the reconstructed images $\varepsilon(r)_{updated}$ in a memory of the computer system.

2. The system of claim 1, wherein the object comprises a biological object with vasculature.

3. The system of claim 1, wherein the processor is further configured to generate synchronization signals corresponding to different phases of a subject's cardiac activity.

4. The system of claim 1, wherein the processor is further configured to:

use one or more radiation cycles required to compile matrices of raw tomographic data corresponding to two or more dielectric states of the object having different dielectric properties of a portion of the object, compile a first matrix of raw data, and compile a second matrix of raw data.

5. The system of claim 4, wherein the object is a blood vessel or lumen.

6. The system of claim 4, wherein the two or more dielectric states correspond to different flow volume of the fluid through said blood vessel or lumen.

7. A system for tomographic imaging of a dielectric object, comprising:

an electromagnetic measurement system configured to acquire electromagnetic (EM) signals and digitize the EM signals, a cardiac activity recording system configured to acquire Electrocardiogram (ECG) signals and digitize the acquired ECG signals, and a computer system with a processor configured to synchronize the EM signals and the ECG signals, reconstruct images or movies of dielectric properties of the object or reconstruct images or movies of angio-dielectric properties of the object, process the reconstructed images or movies of the dielectric properties or the angio-dielectric properties, assess hypoxia and viability of biological tissues based on the post-processed images or movies, and for images $\varepsilon(r)^{ad}_{updated}$ or movies $\varepsilon(r, \text{time})^{ad}_{updated}$ of angio-dielectric properties, the processor is further configured to:

establish parameters and geometric configuration of the EM measurement system, including at least one of frequencies of the EM measurement system used, data acquisition time per acquisition frame, number of frames acquired, dielectric properties of media surrounding the object under the study within an imaging domain, number and position of transmitting antennas of the EM measurement system, and number and position of receiving antennas of the EM measurement system synchronize measurements of the EM signals and measurements of the ECG signals, choose a first and second phase of interest from a cardiac activity cycle, use raw data acquired from electromagnetic measurements system during the first phase, form a matrix of complex EM fields from N transceivers measured on M receivers according to (M*N matrix)–$\text{Sij}^{EXP-1}$, i=1,N; j=1,M;

calibrate and form M*N matrix of calibrated $\text{Sij}^{EXP-1}$ based on first measurement phase data, use raw data acquired from electromagnetic measurements system during the second phase, form a matrix of complex EM fields from N transceivers measured on M receivers according to (M*N matrix)–$\text{Sij}^{EXP-2}$, i=1,N; j=1,M;

calibrate and form M*N matrix of calibrated $\text{Sij}^{EXP-2}$ based on second measurement phase data, calculate perturbated M*N matrix of $\text{Sij}^{EXP \ 1/2}= \text{Sij}^{EXP-1}+\alpha(\text{Sij}^{EXP-1}-\text{Sij}^{EXP-2})/|\text{Sij}^{EXP-1}|$, wherein $|\text{Sij}^{EXP-1}|$ is a norm of complex $\text{Sij}^{EXP-1}$ and $\alpha$—is a parameter chosen by a trial method, iteratively reconstruct an image by using an initial distribution of dielectric properties $\varepsilon_1(r)$ at first iteration, wherein $\varepsilon_1(r)=\varepsilon_0$, where $\varepsilon_0$ is known dielectric properties of outside of an object under the study and within the imaging domain, calculate EM field distribution from N (i=1,N) transceivers within the study domain $E_i(\varepsilon_k(r))$ and on M (j=1,M) receivers $\text{Sij}^{THR}$ at $k^{th}$ iteration (k=1,K), calculate of alteration $\Delta(\varepsilon(r))$ using gradient or/and Newton type of methods in form of:

a) for gradient $\Delta(\varepsilon(r)) \sim \Sigma_{i,j}^{N,M}(E_i{}^*(\varepsilon_k(r)) \times E_j{}^*(\varepsilon_k(r)) \times (Sij^{THR} - Sij^{EXP\ 1/2})$ b) for Newton $\Delta(\varepsilon(r)) \sim$ inversion of the matrix $Dij = (E_i{}^*(\varepsilon_k(r)) \times E_j(\varepsilon_k(r))$;

update a distribution of dielectric properties within the study domain at iteration kas $\varepsilon(r)_{updated} = \varepsilon_{k-1}(r) + \Delta(\varepsilon(r))$, determine if $\varepsilon(r)_{updated}$ satisfies a decision making criteria, in response to determining the decision criteria is satisfied displaying the reconstructed angio-dielectric image $\varepsilon(r)_{updated}$ and further process the image and store the image in a memory of the computer system, in response to determining the decision criteria is not satisfied, take the reconstructed angio-dielectric image $\varepsilon(r)_{updated}$ to the next iteration cycle, wherein the criteria is based on the satisfaction of the following inequation at iteration k: $\Sigma_{i,j}^{N,M} |(Sij^{THR\_iter=k} - Sij^{EXP\ 1/2})| < \beta * \Sigma_{i,j}^{N,M} |(Sij^{THR\_iter=1} - Sij^{EXP\ 1/2})|$, where $|A|$ denotes a norm of complex A and $\beta$ is a convergence accuracy parameter;

provide multiple reconstructed images over time, provide input and control parameters and calculation flow control, and store electromagnetic measurements data, cardiac activity data and reconstructed angio-dielectric images $\varepsilon(r)_{updated}$ in a memory of the computer system.

8. The system of claim 7, wherein for images $\varepsilon(r)^{ad}_{updated}$ or movies $\varepsilon(r,\ time)^{ad}_{updated}$ of angio-dielectric properties, the processor is further configured to calculate a perturbated M*N matrix in the form of $Sij^{EXP1/2} = Sij^{EXP-2} + \beta(Sij^{EXP-2} - Sij^{EXP-1})/|Sij^{EXP-2}|$, where $|Sij^{EXP-2}|$ is a norm of complex $Sij^{EXP-2}$ and $\beta$—is a parameter chosen by a trial method OR in another forms of linear combination of $Sij^{EXP-1}$, $Sij^{EXP-2}$, $|Sij^{EXP-1}|$, $|Sij^{EXP-2}|$, and weighting parameter $\alpha$.

9. The system of claim 7, wherein for images $\varepsilon(r)^{ad}_{updated}$ or movies $\varepsilon(r,\ time)^{ad}_{updated}$ of angio-dielectric properties, the processor is further configured to calculate a perturbated M*N matrix in case when more than two datasets used (for example, K datasets), is calculated as a linear combination of all or portions of K elements $Sij^{EXP-m}$ their norms $|Sij^{EXP-n}|$ and weighting parameters $\alpha_n$ (m=1,K; n=1,K−1).

10. The system of claim 7, wherein the object comprises a biological object with vasculature.

11. The system of claim 7, wherein the processor is further configured to generate synchronization signals corresponding to different phases of a subject's cardiac activity.

12. The system of claim 7, wherein the processor is further configured to:

use one or more radiation cycles required to compile matrices of raw tomographic data corresponding to two or more dielectric states of the object having different dielectric properties of a portion of the object, compile a first matrix of raw data, and compile a second matrix of raw data.

13. The system of claim 12, wherein the object is a blood vessel or lumen.

14. The system of claim 12, wherein the two or more dielectric states correspond to different flow volume of the fluid through said blood vessel or lumen.

\* \* \* \* \*